US011903936B2

(12) United States Patent
Phillips et al.

(10) Patent No.: US 11,903,936 B2
(45) Date of Patent: Feb. 20, 2024

(54) ANTI-MALARIAL AGENTS

(71) Applicants: THE BOARD OF REGENTS OF THE UNIVERSITY OF TEXAS SYSTEM, Austin, TX (US); MMV MEDICINES FOR MALARIA VENTURE, Geneva (CH)

(72) Inventors: Margaret Phillips, Dallas, TX (US); Michael Palmer, Broadstairs (GB); Susan A. Charman, South Melbourne (AU); Karl Shawn Watts, Portland, OR (US); Aleksey I. Gerasyuto, Flemington, NJ (US); Goran Krilov, Long Island City, NY (US)

(73) Assignees: THE BOARD OF REGENTS OF THE UNIVERSITY OF TEXAS SYSTEM, Austin, TX (US); MMV MEDICINES FOR MALARIA VENTURE, Geneva (CH)

(*) Notice: Subject to any disclaimer, the term of this patent is extended or adjusted under 35 U.S.C. 154(b) by 0 days.

(21) Appl. No.: 17/787,378

(22) PCT Filed: Dec. 18, 2020

(86) PCT No.: PCT/EP2020/087166
§ 371 (c)(1),
(2) Date: Jun. 20, 2022

(87) PCT Pub. No.: WO2021/123266
PCT Pub. Date: Jun. 24, 2021

(65) Prior Publication Data
US 2023/0056202 A1    Feb. 23, 2023

Related U.S. Application Data

(60) Provisional application No. 62/951,218, filed on Dec. 20, 2019.

(30) Foreign Application Priority Data

Dec. 24, 2019 (EP) .................................... 19219647

(51) Int. Cl.
| | |
|---|---|
| *C07D 401/14* | (2006.01) |
| *A61P 33/06* | (2006.01) |
| *A61K 31/4439* | (2006.01) |
| *A61K 31/122* | (2006.01) |
| *A61K 31/137* | (2006.01) |
| *A61K 31/155* | (2006.01) |
| *A61K 31/366* | (2006.01) |
| *A61K 31/4196* | (2006.01) |
| *A61K 31/4706* | (2006.01) |
| *A61K 31/4709* | (2006.01) |
| *A61K 31/473* | (2006.01) |
| *A61K 31/4745* | (2006.01) |
| *A61K 31/65* | (2006.01) |
| *C07D 403/12* | (2006.01) |

(52) U.S. Cl.
CPC ........ *A61K 31/4439* (2013.01); *A61K 31/122* (2013.01); *A61K 31/137* (2013.01); *A61K 31/155* (2013.01); *A61K 31/366* (2013.01); *A61K 31/4196* (2013.01); *A61K 31/473* (2013.01); *A61K 31/4706* (2013.01); *A61K 31/4709* (2013.01); *A61K 31/4745* (2013.01); *A61K 31/65* (2013.01); *A61P 33/06* (2018.01); *C07D 401/14* (2013.01); *C07D 403/12* (2013.01)

(58) Field of Classification Search
CPC ............................... C07D 401/14; A61P 33/06
See application file for complete search history.

(56) References Cited

U.S. PATENT DOCUMENTS

| 9,238,653 B2 | 1/2016 | Rathod et al. |
| 2011/0130381 A1 | 6/2011 | Bastos et al. |

FOREIGN PATENT DOCUMENTS

| JP | H04297478 | 10/1992 |
| WO | WO 2010/129208 | 11/2010 |
| WO | WO 2011/041304 | 4/2011 |

OTHER PUBLICATIONS

Datta et al. Crystal structures of drugs: Advances in determination, prediction, and engineering; 2004, Nature Reviews, vol. 3, pp. 42-57.*
JP Patent Application No. 28690434, 1999, pp. 1-49.*
Angulo-Barturen, I. et al. "A Murine Model of *falciparum*-Malaria by In Vivo Selection of Competent Strains in Non-Myelodepleted Mice Engrafted with Human Erythrocytes" *PLoS ONE*, May 21, 2008, pp. 1-14, vol. 3, Issue 5, e2252.
Bennett, T. N. et al. "Novel, Rapid, and Inexpensive Cell-Based Quantification of Antimalarial Drug Efficacy" *Antimicrobial Agents and Chemotherapy*, May 2004, pp. 1807-1810, vol. 48, No. 5.
Booker, M. L. et al. "Novel Inhibitors of *Plasmodium falciparum* Dihydroorotate Dehydrogenase with Anti-malarial Activity in the Mouse Model" *The Journal of Biological Chemistry*, Oct. 22, 2010, pp. 33054-33064, vol. 285, No. 43.
Collins, K. A. et al. "DSM265 at 400 Milligrams Clears Asexual Stage Parasites but Not Mature Gametocytes from the Blood of Healthy Subjects Experimentally Infected with *Plasmodium falciparum*" *Antimicrobial Agents and Chemotherapy*, Apr. 2019 (published Mar. 27, 2019), pp. 1-11, vol. 63, Issue 4, e01837-18.
Coteron, J. M. et al. "Structure-Guided Lead Optimization of Triazolopyrimidine-Ring Substituents Identifies Potent *Plasmodium falciparum* Dihydroorotate Dehydrogenase Inhibitors with Clinical Candidate Potential" *Journal of Medicinal Chemistry*, Jun. 22, 2011, pp. 5540-5561, vol. 54.

(Continued)

*Primary Examiner* — Samira J Jean-Louis
(74) *Attorney, Agent, or Firm* — SALIWANCHIK, LLOYD & EISENSCHENK

(57) ABSTRACT

The present invention is related to new pyrrole derivatives in the manufacture of a medicament for preventing or treating malaria. Specifically, the present invention is related to pyrrole derivatives useful for the preparation of a pharmaceutical formulation for the inhibition of malaria parasite proliferation.

24 Claims, No Drawings

(56) References Cited

OTHER PUBLICATIONS

Deng, X. et al. "Fluorine Modulates Species Selectivity in the Triazolopyrimidine Class of *Plasmodium falciparum* Dihydroorotate Dehydrogenase Inhibitors" *J. Med. Chem.*, May 7, 2014, pp. 5381-5394, vol. 57.

Dickerman, B. K. et al. "Identification of inhibitors that dually target the new permeability pathway and dihydroorotate dehydrogenase in the blood stage of *Plasmodium falciparum*" *Scientific Reports*, Nov. 22, 2016, pp. 1-15, vol. 6, 37502.

Huang, D. et al. "Design, Synthesis, and Acaricidal Activities of Novel Pyrazole Acrylonitrile Compounds" *J. Heterocyclic Chem.*, Mar. 2017 (published online Jul. 13, 2016), pp. 1121-1128, vol. 54.

Jiménez-Díaz, M. B. et al. "Improved Murine Model of Malaria Using *Plasmodium falciparum* Competent Strains and Non-Myelodepleted NOD-*scid IL2R$\gamma^{null}$* Mice Engrafted with Human Erythrocytes" *Antimicrobial Agents and Chemotherapy*, Oct. 2009, p. 4533-4536, vol. 53, No. 10.

Jiménez-Díaz, M. B. et al. "Quantitative Measurement of *Plasmodium*-Infected Erythrocytes in Murine Models of Malaria by Flow Cytometry Using Bidimensional Assessment of SYTO-16 Fluorescence" *Cytometry Part A*, published online Sep. 10, 2008, pp. 225-235, vol. 75A.

Jiménez-Díaz, M. B. et al. "A New In Vivo Screening Paradigm to Accelerate Antimalarial Drug Discovery" *PLoS ONE*, Jun. 25, 2013, pp. 1-12, vol. 8, Issue 6, e66967.

Kokkonda, S. et al. "Isoxazolopyrimidine-Based Inhibitors of *Plasmodium falciparum* Dihydroorotate Dehydrogenase with Antimalarial Activity" *ACS Omega*, Aug. 15, 2018, pp. 9227-9240, vol. 3.

Kokkonda, S. et al. "Lead Optimization of a Pyrrole-Based Dihydroorotate Dehydrogenase Inhibitor Series for the Treatment of Malaria" *J. Med. Chem.*, Apr. 6, 2020, pp. 1-28.

Llanos-Cuentas, A. et al. "Antimalarial activity of single-dose DSM265, a novel plasmodium dihydroorotate dehydrogenase inhibitor, in patients with uncomplicated *Plasmodium falciparum* or *Plasmodium vivax* malaria infection: a proof-of-concept, open-label, phase 2a study" *Lancet Infec Dis*, Jun. 13, 2018, pp. 1-10, vol. 18.

Malmquist, N. A. et al. "Analysis of Flavin Oxidation and Electron-Transfer Inhibition in *Plasmodium falciparum* Dihydroorotate Dehydrogenase" *Biochemistry*, 2008, pp. 2466-2475, vol. 47, No. 8.

Marwaha, A. et al. "Bioisosteric Transformations and Permutations in the Triazolopyrimidine Scaffold to Identify the Minimum Pharmacophore Required for Inhibitory Activity against *Plasmodium falciparum* Dihydroorotate Dehydrogenase" *J. Med. Chem.*, Aug. 9, 2012, pp. 7425-7436, vol. 55.

McCarthy, J. S. et al. "Safety, tolerability, pharmacokinetics, and activity of the novel long-acting antimalarial DSM265: a two-part first-in-human phase 1a/1b randomised study" *Lancet Infec Dis*, Mar. 28, 2017, pp. 1-10, vol. 17.

McCarthy, J. S. et al. "A Single-Dose Combination Study with the Experimental Antimalarials Artefenomel and DSM265 to Determine Safety and Antimalarial Activity against Blood-Stage *Plasmodium falciparum* in Healthy Volunteers" *Antimicrobial Agents and Chemotherapy*, Dec. 20, 2019, pp. 1-10, vol. 64, Issue 1, e01371-19.

Munier-Lehmann, H. et al. "On Dihydroorotate Dehydrogenases and Their Inhibitors and Uses" *J. Med. Chem.*, Mar. 1, 2013, pp. 3148-3167, vol. 56.

Murphy, S. C. et al. "A Randomized Trial Evaluating the Prophylactic Activity of DSM265 Against Preerythrocytic *Plasmodium falciparum* Infection During Controlled Human Malarial Infection by Mosquito Bites and Direct Venous Inoculation" *The Journal of Infectious Diseases*, 2018 (published online Dec. 5, 2017), pp. 693-702, vol. 217.

Palmer, M. J. et al. "Potent Antimalarials with Development Potential Identified by Structure-Guided Computational Optimization of a Pyrrole-Based Dihydroorotate Dehydrogenase Inhibitor Series" *J. Med. Chem.*, 2021, pp. 1-52, vol. 9.

Phillips, M. A. et al. "Triazolopyrimidine-Based Dihydroorotate Dehydrogenase Inhibitors with Potent and Selective Activity against the Malaria Parasite *Plasmodium falciparum*" *J. Med. Chem.*, 2008, pp. 3649-3653, vol. 51, No. 12.

Phillips, M. A. et al. "Plasmodium Dihydroorotate Dehydrogenase: A Promising Target for Novel Anti-Malarial Chemotherapy" *Infectious Disorders—Drug Targets*, 2010, pp. 226-239, vol. 10. No. 3.

Phillips, M. A. et al. "A long-duration dihydroorotate dehydrogenase inhibitor (DSM265) for prevention and treatment of malaria" *Sci Transl Med.*, Jul. 15, 2015, pp. 1-12, vol. 7, Issue 296, 296ra111.

Phillips, M. A. et al. "A triazolopyrimidine-based dihydroorotate dehydrogenase inhibitor (DSM421) with improved drug-like properties for treatment and prevention of malaria" *ACS Infect Dis.*, Dec. 9, 2016, pp. 1-33, vol. 2, No. 12.

Russell, B. M. et al. "Simple In Vitro Assay for Determining the Sensitivity of *Plasmodium vivax* Isolates from Fresh Human Blood to Antimalarials in Areas where *P. vivax* is Endemic" *Antimicrobial Agents and Chemotherapy*, Jan. 2003, pp. 170-173, vol. 47, No. 1.

Sandtorv, A. H. et al. "Stille Cross-Coupling for the Functionalization of the Imidazole Backbone: Revisit, Improvement, and Applications of the Method" *Eur. J. Org. Chem.*, 2015, pp. 3506-3512.

Skerlj, R. T. et al. "Optimization of Potent Inhibitors of *P. falciparum* Dihydroorotate Dehydrogenase for the Treatment of Malaria" *ACS Med. Chem. Lett.*, Jul. 11, 2011, pp. 708-713, vol. 2.

Srinivasan, P. et al. "Disrupting malaria parasite AMA1-RON2 interaction with a small molecule prevents erythrocyte invasion" *Nature Communications*, Aug. 2, 2013, pp. 1-9, vol. 4, No. 2261.

Sulyok, M. et al. "DSM265 for *Plasmodium falciparum* chemoprophylaxis: a randomised, double blinded, phase 1 trial with controlled human malaria infection" *Lancet Infect Dis.*, Mar. 28, 2017, pp. 1-9, vol. 17.

Wells, T. N. C. et al. "Malaria medicines: a glass half full?" *Nature Reviews Drug Discovery*, Jun. 2015 (published online May 22, 2015), pp. 424-442, vol. 14, No. 6.

White, J. et al. "Identification and Mechanistic Understanding of Dihydroorotate Dehydrogenase Point Mutations in *Plasmodium falciparum* that Confer in Vitro Resistance to the Clinical Candidate DSM265" *ACS Infect. Dis.*, 2018, pp. 1-12, vol. 5, No. 1.

Written Opinion in International Application No. PCT/EP2020/087166, dated Mar. 12, 2021, pp. 1-9.

* cited by examiner

ANTI-MALARIAL AGENTS

STATEMENT REGARDING FEDERALLY SPONSORED RESEARCH

This invention was made with government support under AI103947 awarded by the National Institutes of Health. The government has certain rights in the invention.

CROSS-REFERENCE TO RELATED APPLICATION

This application is the U.S. national stage application of International Patent Application No. PCT/EP2020/087166, filed Dec. 18, 2020.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum*: is the dominant species in sub-Saharan Africa, and is responsible for almost 1 million deaths each year. The disease burden is heaviest in African children under 5 years of age and in pregnant women. *Plasmodium vivax* causes 25-40% of the global malaria burden, particularly in South and Southeast Asia, and Central and South America. The other three main species that are known to infect humans are *Plasmodium ovale*, *Plasmodium malariae* and *Plasmodium knowlesi*.

Malaria is a disease that is prevalent in many developing countries. Approximately 40% of the world's population lives in countries where the disease is endemic; approximately 247 million people suffer from the disease every year.

Various chemical agents have been developed for the treatment and prevention of malaria over the past 20 years (Wells et al., 2015, *Nature Reviews Drug Discovery* 14, 424-442). However, many of these medications are costly and some exhibit significant toxicity and undesirable side effects in humans. Drugs used for treating malaria include artemisinin and its derivatives (such as artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, ferroquine, tafenoquine, arterolane, Spiro[3H-indole-3,1'-[1H]pyrido[3,4-b]indol]-2 (1H)-one, 5,7'-dichloro-6'-fluoro-2',3',4',9'-tetrahydro-3'-methyl-,(1'R,3'S)—](CAS Registry Number: 1193314-23-6), 2-(1,1-difluoroethyl)-5-methyl-N-[4-(pentafluoro-$\lambda^6$-sulfanyl)phenyl]-[1,2,4]triazolo[1,5-a]pyrimidin-7-amine (CAS Registry Number: 1282041-94-4), Morpholine, 4-[2-(4-cis-dispiro[cyclohexane-1,3'-[1,2,4]trioxolane-5',2"-tricyclo[3.3.1.13,7]decan]-4-ylphenoxy) ethyl]-](CAS Registry Number: 1029939-86-3).

However, the widespread emergence of drug resistance of malaria parasites in many tropical countries has compromised many of the current chemotherapies and there is a continued need for new chemotherapeutic approaches.

*P. falciparum* is transmitted to humans via the bite of an infected female *anopheles* mosquito. In humans, the parasite undergoes one cycle of asexual multiplication in hepatocytes, followed by several cycles of infection and multiplication in red blood cells. If the hepatocytic stage is asymptomatic, the erythrocytic stage comprises the destruction of the host erythrocytes, resulting in anemia leading to death, in absence of treatment. Purine metabolism holds significant promise as a target for drug development.

It has long been recognized that *Plasmodium* parasites lack the ability to metabolize exogenous pyrimidines and instead are entirely dependent on de novo pyrimidine biosynthesis to provide precursors for DNA and RNA synthesis, and hence for proliferation. The parasite does not have pyrimidine nucleoside or base salvage pathways, thus the enzymes in the de novo pathway are essential to parasite survival. In contrast, mammalian cells have salvage pathways that provide an alternative route to these essential metabolites.

Dihydroorotate dehydrogenase (DHODH) is an essential enzyme of the pyrimidine salvage pathway, and a number of studies suggest that it is an important target for the development of new chemotherapy against malaria. DHODH is a flavin-dependent mitochondrial enzyme that catalyzes the flavin mononucleotide (FMN)-dependent oxidation of dihydroorotate to orotic acid, an essential step in de novo pyrimidine biosynthesis. Both human and malaria DHODH are mitochondrial enzymes, but X-ray structural analysis has shown that if the overall fold is well-conserved, the presumptive CoQ binding site is variable between species. An inhibitor of human DHODH (HsDHODH) (teriflunomide (A77 1726), the active metabolite of leflunomide is clinically approved for the treatment of rheumatoid arthritis and multiple sclerosis, and a number of compounds have been described that either bind potently to the human enzyme (e.g., brequinar and C41) or selectively inhibit DHODH from various microbial species, demonstrating that DHODH is a druggable target (Miller et al., 2013, *Nat. Med.*, 19, 156-67; Munier-Lehmann et al., 2013, *J. Med. Chem.*, 56, 3148-3167; Phillips et al., 2010, *Infect. Disord. Drug Targets*, 10, 226-239). Triazolopyrimidine-based (e.g. DSM265 and DSM267), imidazo[1,2-a]pyrimidine-based inhibitors of *P. falciparum* dihydroorotate dehydrogenase that inhibit parasite in vitro growth with similar activity have been developed (Philips et al., 2008, *J. Med. Chem.*, 51, 3649-3653; Marwaha et al., 2012, *J. Med. Chem.*, 55, 7425-7436; WO 2011041304; Deng et al., 2014, *J. Med. Chem.*, 57, 5381-5394; Coteron et al., 2011, *J. Med. Chem.*, 54, 5540-5561; Phillips et al, 2015, *Sci Transl Med*, 7(296) 296ra111.doi:10.1126 scitranslmed.aaa6645), and importantly one of these compounds DSM265 reached clinical development for the treatment of malaria showing efficacy for both clinical treatment and for chemoprevention of *P. falciparum* malaria after administration of a single dose of 400 mg (McCarthy, et al., 2017, *Lancet Infec Dis*, 17, 626-635; Llanos-Cuentas, et al., 2018, *Lancet Infec Dis*, 18, 874-883; Sulyok, et al., 2017, *Lancet Infec Dis*, 17, 636-644; Murphy, et al, 2018, *J Infect Dis*, 217, 693-702; Collins, et al, 2019, *Antimicrob Agents Chemother*, 63(4). pii:e01837-18, doi:10.1128 AAC.01837-18; McCarthy, et al., 2019, *Antimicrob Agents Chemother*, doi: 10.1128 AAC.01371-19). These data provide clinical validation of DHODH as a target for the development of antimalarials. However, a clinical study showed that DSM265 (2-(1,1-difluoroethyl)-5-methyl-N-[4-(pentafluoro-$\lambda^6$-sulfanyl)phenyl]-[1,2,4]triazolo[1,5-a]pyrimidin-7-amine) is less effective for the treatment of *P. vivax* malaria, thus limiting its use to *P.* falciparum (Llanos-Cuentas, et al., 2018, supra). Thiophene based compounds that inhibit PfDHODH (Genz 667348) have also been described (Skerlj et al., 2011, *ACSMed. Chem. Lett.*, 2, 708-713; US 2011/0130381) as well as inhibitors that dually target the permeability pathway and DHODH in the blood stage of *Plasmodium falciparum* (Dickerman et al., 2016, *Scientific Reports*, 6, 37502). Genz 667348 reached animal testing but lacked sufficient metabolic stability to support a single dose treatment in humans, while compounds reported to have dual permeability/DHODH activity were only studied in vitro.

Various chemical agents have been developed for the treatment and prevention of malaria over the past 20 years (Wells et al., 2015, *Nature Reviews Drug Discovery* 14, 424-442). However, widespread emergence of drug resistance of malaria parasites in endemic countries has compromised many of the current chemotherapies and there is a continued need for new chemotherapeutic approaches.

SUMMARY OF THE INVENTION

The present invention is directed towards novel pyrrole derivatives which are useful in the treatment and/or prophylaxis of malaria, pharmaceutical formulation, use and manufacture thereof. It has been found that those compounds unexpectedly present several advantages over current clinical candidate DSM265.

A first aspect of the invention provides a compound according to the invention or a pharmaceutically acceptable salt thereof or a pharmaceutically active derivative thereof.

Another aspect of the invention relates to a compound or a pharmaceutically acceptable salt thereof or a pharmaceutically active derivative thereof according to the invention for use as a medicament.

Another aspect of the invention relates to a compound according to the invention or a pharmaceutically acceptable salt thereof or a pharmaceutically active derivative thereof for use in the prevention and/or treatment of malaria.

Another aspect of the invention relates to the use of a compound according to the invention or a pharmaceutically acceptable salt thereof or a pharmaceutically active derivative thereof for the preparation of a pharmaceutical composition for the prevention and/or treatment of malaria.

Another aspect of the invention resides in a pharmaceutical formulation comprising at least one compound according to the invention or a pharmaceutically acceptable salt thereof or a pharmaceutically active derivative thereof and a pharmaceutically acceptable carrier, diluent or excipient thereof.

Another aspect of the invention resides in a method for preventing and/or treating malaria in a subject. The method comprises administering a compound according to the invention or a pharmaceutically acceptable salt thereof or a pharmaceutically active derivative thereof in a subject in need thereof.

Another aspect of the invention provides a process for the preparation of a compound according to the invention or a pharmaceutically acceptable salt thereof or a pharmaceutically active derivative thereof according to the invention and intermediates thereof.

Another aspect of the invention provides a process for the preparation of a compound of Formula (I) comprising a step of transforming an intermediate of Formula (X) or Formula (XI).

Another aspect of the invention provides an intermediate of Formula (X) or of Formula (XI) according to the invention.

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "$C_1$-$C_6$ alkyl" when used alone or in combination with other terms, comprises a straight chain or branched $C_1$-$C_6$ alkyl which refers to monovalent alkyl groups having 1 to 6 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, and the like.

The term "$C_2$-$C_6$ alkenyl" when used alone or in combination with other terms, comprises a straight chain or branched $C_2$-$C_6$ alkenyl. Particularly, it refers to groups having 2 to 6 carbon atoms and having at least 1 or 2 sites of alkenyl unsaturation. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like. Among others, are vinyl or ethenyl (—CH═$CH_2$), n-2-propenyl (allyl, —$CH_2$CH═$CH_2$), isopropenyl, 1-propenyl, 2-methyl-1-propenyl, 1-butenyl, 2-butenyl, and 3-methyl-2-butenyl and the like. The term "$C_2$-$C_6$ alkynyl" when used alone or in combination with other terms, comprises a straight chain or branched $C_2$-$C_6$ alkynyl. It may have any available number of triple bonds in any available positions. This term is exemplified by groups such as alkynyl groups that may have a carbon number of 2-6, and optionally a double bond, such as ethynyl (—C≡CH), 1-propynyl, 2-propynyl (propargyl: —$CH_2$C≡CH), 2-butynyl, 2-pentene-4-ynyl, and the like. The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "monocyclic aryl" refers to an unsaturated aromatic carbocyclic group of from 6 to 14 carbon atoms having a single ring (e.g. phenyl).

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, isoquinolinyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "5-membered heterocycle" refers to a 5-membered heteroaryl or a 5-membered heterocycloalkyl. Examples of those include triazole, pyrazole, triazole, imidazole, and isoxazole.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_2$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g. cyclohexyl) or multiple condensed rings (e.g. norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl) methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl," "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to alkyl groups having an acyloxy substituent, including 2-(ethylcarbonyloxy)ethyl and the like.

The term "alkoxy" refers to the group —O—R where R includes optionally substituted "$C_1$-$C_6$ alkyl", optionally substituted "aryl", optionally substituted "heteroaryl", optionally substituted "aryl $C_1$-$C_6$ alkyl" or optionally substituted "heteroaryl $C_1$-$C_6$ alkyl". The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to $C_1$-$C_6$ alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_6$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R and R" are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_2$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$-alkyl groups having an ureido substituent, including 2-(N'-methylureido)ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "$C_3$-

$C_8$-cycloalkyl," or "heterocycloalkyl," and where R and R', together with the nitrogen atom to which they are attached, can optionally form a 3-8-membered heterocycloalkyl ring.

The term "amino $C_1$-$C_6$ alkyl" refers to alkyl groups having an amino substituent, including 2-(1-pyrrolidinyl) ethyl and the like.

The term "ammonium" refers to a positively charged group —N$^+$RR'R" where R, R' and R" are independently "$C_1$-$C_6$ alkyl", "$C_1$-$C_6$ alkyl aryl", "$C_1$-$C_6$ alkyl heteroaryl," "$C_3$-$C_8$-cycloalkyl," or "heterocycloalkyl," and where R and R', together with the nitrogen atom to which they are attached, can optionally form a 3-8-membered heterocycloalkyl ring.

The term "ammonium $C_1$-$C_6$ alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "$C_2$-$C_6$ $C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfamate" refers to a group —OSO$_2$—NRR' wherein R and R' are independently selected from H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and the like.

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl)ethyl and the like.

The term "sulfinyl" refers to a group "—S(O)—R" wherein R is selected from "$C_1$-$C_6$ alkyl," "$C_1$-$C_6$ alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl $C_1$-$C_6$ alkyl" refers to alkyl groups having a sulfinyl substituent, including 2-(methylsulfinyl) ethyl and the like.

The term "sulfanyl" refers to groups —S—R where R includes H, halogens, e.g. a —SF$_5$ group, optionally substituted "$C_1$-$C_6$ alkyl," in particular "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "$C_3$-$C_8$-cycloalkyl $C_1$-$C_6$ alkyl," or "heterocycloalkyl $C_1$-$C_6$ alkyl".

The term "sulfanyl $C_1$-$C_6$ alkyl" refers to $C_1$-$C_5$-alkyl groups having a sulfanyl substituent, including 2-(ethylsulfanyl)ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —SO$_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl $C_3$-$C_8$-cycloalkyl," "$C_1$-$C_6$ alkyl heterocycloalkyl," "acyl", "amino," "amide", "aminosulfonyl," "ammonium," "acyl amino," "aminocarbonyl," "aryl," "heteroaryl," "sulfinyl," "sulfonyl," "sulphonamide", "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the compounds according to the invention. Examples of such salts are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, methane sulfonic acid, p-toluene sulfonic acid and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting anti-malarial activity that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g. by oxidation, reduction, hydrolysis or the like, each of which is carried out enzymatically. These compounds can be produced from compounds of the present invention according to well-known methods.

The term "indirectly" also encompasses metabolites of compounds according to the invention. The term "metabolite" refers to all molecules derived from any of the compounds according to the present invention in a cell or organism, preferably mammal.

In the context of the present invention are encompassed pharmaceutically acceptable salts, hydrates, solvates, or polymorphs and pharmaceutically active derivatives of compounds of the invention.

The term "malaria" includes disease and conditions related to an infection by Plasmodium.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive phophylaxis is used whereas against *P. vivax* or a combination of *P. falciparum* and *P. vivax*, terminal prophylaxis is used.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like.

Compounds

According to one embodiment, is provided a compound according to Formula (I):

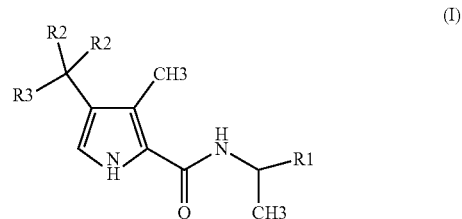

wherein $R_1$ is an optionally substituted 5-membered heterocycle such as an optionally substituted triazole, such as optionally substituted 1, 2, 4 triazole (e.g. 1, 2, 4 triazole), or optionally substituted pyrazole (1H-pyrazole-5-carboxamide) such as optionally substituted pyrazole-4-yl (e.g. 1H-pyrazol-4-yl, 1-methyl-pyrazol-4-yl) or optionally substituted pyrazole-3-yl (e.g. 5-methyl-1H-pyrazol-3yl, 5-cyano-1H-pyrazol-3-yl) or an optionally substituted imidazole such as an optionally substituted imidazole-4-yl (e.g. imidazole-4-yl) or an optionally substituted isoxazole such as an optionally substituted isoxazol-3-yl (e.g. 5-methyl-isoxazol-3-yl); $R_2$ is H or both $R_2$ are joined to form an optionally substituted cyclopropyl and $R_3$ is selected from an optionally substituted monocyclic aryl such as an optionally substituted phenyl (e.g. 3-fluoro-4-(trifluoromethyl)phenyl or 3-cyano-4-(trifluoromethyl)phenyl) and an optionally substituted heteroaryl such as optionally substituted pyridinyl, for example optionally substituted pyridin-3-yl (e.g. trifluoromethyl) pyridin-3-yl, di-fluoro-methyl pyridin-3-yl; as well as pharmaceutically acceptable salts, hydrates, solvates, tautomers, polymorphs, racemic mixtures, optically active forms and pharmaceutically active derivative thereof.

In a particular embodiment, the invention provides a compound according to the invention wherein $R^1$ is an optionally substituted triazole, such as optionally substituted 1, 2, 4 triazole (e.g. 1, 2, 4 triazole).

In another particular embodiment, the invention provides a compound according to the invention wherein $R^1$ is an optionally substituted pyrazole (e.g. 1H-pyrazole-5-carboxamide) such as optionally substituted pyrazole-4-yl (e.g. 1H-pyrazol-4-yl, 1-methyl, pyrazol-4-yl) or optionally substituted pyrazole-3-yl (e.g. 5-methyl-1H-pyrazol-3yl, 5-cyano-1H-pyrazol-3-yl).

In another particular embodiment, the invention provides a derivative according to the invention wherein $R^1$ is an optionally substituted imidazole such as an optionally substituted imidazole-4-yl (e.g. imidazole-4-yl).

In another particular embodiment, the invention provides a compound according to the invention wherein $R^1$ is an optionally substituted isoxazole such as an optionally substituted isoxazol-3-yl (e.g. 5-methylisoxazol-3-yl).

In another particular embodiment, the invention provides a compound according to the invention wherein $R^2$ is H.

In another particular embodiment, the invention provides a compound according to the invention wherein both $R_2$ are joined to form an optionally substituted cyclopropyl (e.g. cyclopropyl).

In another particular embodiment, the invention provides a compound according to the invention wherein $R^3$ is an optionally substituted monocyclic aryl such as an optionally substituted phenyl (e.g. 3-fluoro-4-(trifluoromethyl)phenyl).

In a particular embodiment, $R^3$ has the following formula $R_a$:

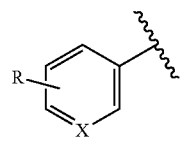

(Ra)

wherein R represents 1 to 4 optional substituents, such as 1 optional substituent, said substituent being independently selected from the following group of substituents, all being further optionally substituted: "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl $C_3$-$C_8$-cycloalkyl," "$C_1$-$C_6$ alkyl heterocycloalkyl," "acyl", "amino," "amide", "aminosulfonyl," "ammonium," "acyl amino," "aminocarbonyl," "aryl," "heteroaryl," "sulfinyl," "sulfonyl," "sulphonamide", "alkoxy," "alkoxy carbonyl," "carbamate," "sulfanyl," "halogen," trihalomethyl, dihalomethyl, cyano, hydroxy, mercapto and nitro and X is selected from N and $CR^4$, $R^4$ being selected from H, halogen (e.g. fluoro) and cyano.

In a further particular embodiment, at least one R is an optionally substituted $C_1$-$C_6$ alkyl such as CHF2 or CF3.

In a further particular embodiment, at least one R is a halogen (e.g. Fluoro).

In another further particular embodiment, at least one R is cyano.

In another further particular embodiment, $R^3$ is of Formula ($R_a$) and is substituted in para position (e.g. monosubstituted).

In another further particular embodiment, $R^4$ is H.

In another particular embodiment, the invention provides a compound according to the invention wherein $R^3$ is an optionally substituted heteroaryl such as optionally substituted pyridinyl, pyridinyl optionally substituted with halogen or with optionally substituted $C_1$-$C_6$ alkyl, for example optionally substituted pyridin-3-yl (e.g. trifluoromethyl pyridin-3-yl, difluoromethyl pyridin-3-yl.

In a particular embodiment is provided a compound selected from the following group:
3-methyl-N-(1-(1H-1,2,4-triazol-3-yl)ethyl)-4-(1-(6-(trifluoromethyl)pyridin-3-yl) cyclopropyl)-1H-pyrrole-2-carboxamide;
N-(1-(1H-1,2,4-triazol-3-yl)ethyl)-4-(3-fluoro-4-(trifluoromethyl)benzyl)-3-methyl-1H-pyrrole-2-carboxamide;
N-(1-(1H-pyrazol-4-yl)ethyl)-3-methyl-4-(1-(6-(trifluoromethyl)pyridin-3-yl)cyclopropyl)-1H-pyrrole-2-carboxamide;
3-methyl-N-[1-(5-methyl-1H-pyrazol-3-yl)ethyl]-4-{1-[6-(trifluoromethyl)pyridine-3-yl]cyclopropyl}-1H-pyrrole-2-carboxamide;
3-(1-(3-methyl-4-(1-(6-(trifluoromethyl)pyridin-3-yl)cyclopropyl)-1H-pyrrole-2-carboxamido)ethyl)-1H-pyrazole-5-carboxamide;
N-(1-(5-cyano-1H-pyrazol-3-yl)ethyl)-3-methyl-4-(1-(6-(trifluoromethyl)pyridin-3-yl) cyclopropyl)-1H-pyrrole-2-carboxamide;
N-(1-(1H-imidazol-4-yl)ethyl)-3-methyl-4-(1-(6-(trifluoromethyl)pyridin-3-yl)cyclopropyl)-1H-pyrrole-2-carboxamide;
4-(1-(6-(difluoromethyl)pyridin-3-yl)cyclopropyl)-3-methyl-N-(1-(1H-1,2,4-triazol-3-yl) ethyl)-1H-pyrrole-2-carboxamide;
4-{1-[3-cyano-4-(trifluoromethyl)phenyl]cyclopropyl}-3-methyl-N-[1-(1H-1,2,4-triazol-3-yl) ethyl]-1H-pyrrole-2-carboxamide;
3-methyl-N-(1-(5-methylisoxazol-3-yl)ethyl)-4-((6-(trifluoromethyl)pyridin-3-yl)methyl)-1H-pyrrole-2-carboxamide;
3-methyl-N-(1-(1H-pyrazol-4-yl)ethyl)-4-((6-(trifluoromethyl)pyridin-3-yl)methyl)-1H-pyrrole-2-carboxamide; and
3-methyl-N-(1-(1-methyl-1H-pyrazol-4-yl)ethyl)-4-((6-(trifluoromethyl)pyridin-3-yl)methyl)-1H-pyrrole-2-carboxamide; as well as pharmaceutically acceptable salts, hydrates, solvates, tautomers, polymorphs, racemic mixtures, optically active forms and pharmaceutically active derivative thereof.

In a further particular embodiment is provided a enantiomer of a compound according to the invention which is in configuration R.

In a further particular embodiment is provided a enantiomer of a compound according to the invention which is in configuration S.

The compounds of the invention are useful in the manufacture of a medicament for the prevention or treatment of malaria, are capable of killing and/or inhibiting malaria parasite replication.

Compositions

The invention provides pharmaceutical compositions useful for the prophylaxis or treatment of malaria. The invention further provides methods for treating a mammalian patient, and most preferably a human patient, who is suffering from malaria.

In another particular embodiment, is provided a pharmaceutical formulation containing at least one derivative according the invention and a pharmaceutically acceptable carrier, diluent or excipient thereof.

In another particular embodiment, is provided a pharmaceutical formulation comprising a compound according to Formula (I) and a further antimalarial agent as defined in the detailed description.

In another particular embodiment, is provided a pharmaceutical formulation comprising a compound according to Formula (I) and at least one further antimalarial agent selected from artemisinin and its derivatives such as artemether, artesunate, dihydroartemisinin, chloroquine, hydroxychloroquine, quinine, mefloquine, amodiaquine, atovaquone/proguanil, doxycycline, clindamycin, halofantrine, lumefantrine, pyronaridine, pyrimethamine-sulfadoxine, ferroquine, tafenoquine, piperaquine and primaquine, Spiro[3H-indole-3,1'-[1H]pyrido[3,4-b]indol]-2(1H)-one, 5,7'-dichloro-6'-fluoro-2',3',4',9'-tetrahydro-3'-methyl-, (1'R, 3'S)— (CAS Registry Number: 1193314-23-6), 2-(1,1-difluoroethyl)-5-methyl-N-[4-(pentafluoro-$\lambda^6$-sulfanyl)phenyl]-[1,2,4]triazolo[1,5-a]pyrimidin-7-amine (CAS Registry Number: 1282041-94-4), [3,3'-Bipyridin]-2-amine, 5-[4-(methylsulfonyl)phenyl]-6'-(trifluoromethyl)-(CAS Registry Number: 1314883-11-8) and Ethanone, 2-amino-1-[2-(4-fluorophenyl)-3-[(4-fluorophenyl)amino]-5,6-dihydroimidazo[1,2-a]pyrazin-7(8H)-yl]-(CAS Registry Number 1261109-90-3).

Pharmaceutical compositions of the invention can contain one or more compound(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. Compositions according to the invention are preferably oral.

Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in out in Part 5 of *Remington's "The Science and Practice of Pharmacy"*, 22nd Edition, 2012, University of the Sciences in Philadelphia, Lippincott Williams & Wilkins, which is incorporated herein by reference. Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, vaginally, rectally, transmucosally, topically, via inhalation, via buccal or intranasal administration, or combinations thereof Parenteral administration includes, but is not limited to, intravenous, intra-arterial, intra-peritoneal, subcutaneous, intramuscular, intrathecal, and intra-articular. The compositions of this invention may also be administered in the form of an implant, which allows slow release of the compositions as well as a slow controlled i.v. infusion. In a preferred embodiment, compounds according to the invention are administered orally.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to the invention, the compounds of the invention and pharmaceutical formulations thereof can be administered alone or in combination with a co-agent useful in the treatment of malaria, such as substances useful in the treatment and/or prevention of malaria e.g. for example a co-agent including, but not limited to, artemisinin and its derivatives such as artemether, artesunate, dihydroartemisinin, chloroquine, hydroxychloroquine, quinine, mefloquine, amodiaquine, atovaquone/proguanil, doxycycline, clindamycin, halofantrine, lumefantrine, pyronaridine, pyrimethamine-sulfadoxine, ferroquine, tafenoquine, piperaquine and primaquine.

Further co-agents useful in combination with the compounds of the invention are selected from Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)— (CAS Registry Number: 1193314-23-6), 2-(1,1-difluoroethyl)-5-methyl-N-[4-(pentafluoro-26-sulfanyl)phenyl]-[1,2,4]triazolo[1,5-a]pyrimidin-7-amine (CAS Registry Number: 1282041-94-4), [3,3'-Bipyridin]-2-amine, 5-[4-(methylsulfonyl)phenyl]-6'-(trifluoromethyl)-(CAS Registry Number: 1314883-11-8), Ethanone, 2-amino-1-[2-(4-fluorophenyl)-3-[(4-fluorophenyl)amino]-5,6-dihydroimidazo[1,2-a]pyrazin-7(8H)-yl]-(CAS Registry Number 1261109-90-3).

The invention encompasses the administration of a compound according to the invention or of a pharmaceutical formulation thereof, wherein the compounds of the invention or the pharmaceutical formulation thereof are administered to an individual prior to, simultaneously or sequentially with other therapeutic regimens or co-agents useful in the treatment of malaria (e.g. multiple drug regimens), in an effective amount. Compounds of the invention or the pharmaceutical formulations thereof that are administered simultaneously with said co-agents can be administered in the same or different composition(s) and by the same or different route(s) of administration.

Patients

In an embodiment, patients according to the invention are patients suffering from malaria.

In another embodiment, patients according to the invention are patients with a high risk of being infected by *Plasmodium*.

In another embodiment, patients according to the invention are patients with a high risk of being infected by *Plasmodium falciparum*.

In another embodiment, patients according to the invention are patients with a high risk of being infected by *Plasmodium vivax*.

In another embodiment, patients according to the invention are patients with a high risk of being infected by *Plasmodium ovale*.

In another embodiment, patients according to the invention are patients with a high risk of being infected by *Plasmodium malariae*.

In another embodiment, patients according to the invention are patients with a high risk of being infected by *Plasmodium knowlesi*.

USE ACCORDING TO THE INVENTION

In one embodiment, the invention provides a compound according to Formula (I) as well as pharmaceutically acceptable salts, hydrates, solvates, or polymorphs, and pharmaceutically active derivative thereof for the treatment or prophylaxis of malaria.

In another embodiment, the invention provides a method for preventing or treating malaria in a subject. The method comprises administering an effective amount of a compound according to the invention, or a pharmaceutically acceptable salt or a pharmaceutically active derivative thereof or a pharmaceutical formulation thereof in a subject in need thereof.

In another embodiment, the invention provides a use of a compound or a method according to the invention wherein the compound is to be administered in combination with a co-agent useful in the treatment of malaria.

In another embodiment, the invention provides a pharmaceutical composition comprising a compound according to the invention in combination with a co-agent useful in the treatment of malaria.

In another embodiment, the invention provides a process for the preparation of a compound according to the invention comprising the step of transforming a compound according to Formula (X) into a compound of Formula (Ia), i.e. a compound of Formula (I), wherein both $R_2$ are joined to form an optionally substituted cyclopropyl to lead to a compound of Formula (Ia) as described under Scheme 1 below:

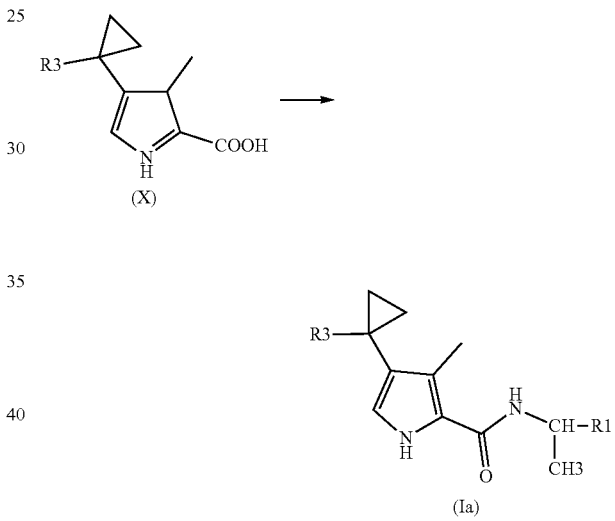

Scheme 1 wherein $R^1$ and $R^3$ are as defined herein.

According to a particular embodiment, this method according to the invention includes conditions suitable for the formation of an activated ester intermediate from the carboxylic acid (XI) followed by reaction with the amine derivative, e.g. use of HATU (1-[Bis(dimethylamino)methylene]-1H-1,2,3-triazolo[4,5-b]pyridinium3-oxide-hexafluoro phosphate) or other established peptide coupling reagents such as DCC and related carbodiimide reagents, CDI, or anhydride formation with a chloroformate reagent. For a comprehensive range of amide bond formation methods (*Comprehensive Organic Transformations: A Guide to Functional Group Preparations* 4 *Volume Set:* 1-2 Edited by Richard C. Larock).

In another embodiment, the invention provides a process for the preparation of a compound according to the invention comprising the step of transforming a compound according to Formula (XI) in a compound of Formula (Ib), i.e. a compound of Formula (I), wherein both $R_2$ are H to lead to a compound of Formula (Ib) as described under Scheme 2 below:

17

Scheme 2

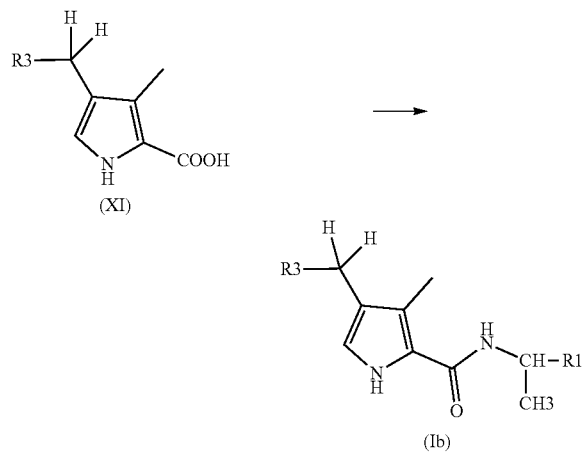

wherein R¹ and R³ are as defined herein.

In another further embodiment, the invention provides an intermediate of Formula (X), as defined herein, in particular the following compounds:
3-methyl-4-(1-(6-(trifluoromethyl)pyridin-3-yl)cyclopropyl)-1H-pyrrole-2-carboxylic acid (9a);
4-(3-fluoro-4-(trifluoromethyl)benzyl)-3-methyl-1H-pyrrole-2-carboxylic acid (9b) and
4-(1-(6-(difluoromethyl)pyridin-3-yl)cyclopropyl)-3-methyl-1H-pyrrole-2-carboxylic acid (9c).

In another further embodiment, the invention provides an intermediate of Formula (XI), as defined herein, in particular 3-methyl-4-((6-(trifluoromethyl)pyridin-3-yl)methyl)-1H-pyrrole-2-carboxylic acid (12a).

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. In the following the present invention shall be illustrated by means of some examples, which are not to be viewed as limiting the scope of the invention.

EXAMPLES

The following abbreviations refer respectively to the definitions below:
RT (room temperature), Ag₂CO₃ (Silver Carbonate), NMP (N-methylpyrrolidone), NaH (Sodium Hydride), CH₂Cl₂ (Dichloromethane), TsCl (4-Methylbenzene-1-sulfonyl Chloride), DMF (Dimethylformamide), MeMgBr (Methylmagnesium Bromide), ᵗBuOK (Potassium tert-Butoxide), Et₃N (Triethylamine), NaOH (Sodium Hydroxide), EtOH Ethanol), EtOAc (Ethyl Acetate), NaHCO₃(Sodium Bicarbonate), Na₂SO₄ (Sodium Sulphate), Na₂S₂O₃ (Sodium Thiosulfate), DIPEA (Di-isopropylethylamine), K₃PO₄ (Tripotassium Phosphate), Pd(OAc)₂ (Palladium Acetate), DMSO (Dimethyl Sulfoxide), HATU (1-[Bis(dimethylamino)methylene]-1H-1,2,3-triazolo[4,5-b]pyridinium3-oxide hexafluorophosphate), MS (Mass Spectrometry), NMR (Nuclear magnetic resonance), TBAF (Tetra-n-butylammonium fluoride); TFA (Trifluoroacetic acid), THF (Tetrahydrofuran), TLC (Thin layer chromatography).

The compounds of invention have been named according to the IUPAC standards used in the program ChemAxon Marvin Sketch (Version 16.8.15.0).

18

All reagents and starting materials were obtained from commercial suppliers and used without further purification. 1-propynylmagnesium bromide (0.5M in THF) and Ag₂CO₃ were purchased from Sigma-Aldrich. Dess Martin and ethyl isocyanoacetate were purchased from Spectrochem. 5-Amino-2-trifluoromethylpyridine was purchased from Combi-Blocks, Inc. CA, USA. For all compounds, reaction progress was monitored by thin layer chromatography (TLC) on preloaded silica gel 60 F254 plates. Visualization was achieved with UV light and iodine vapor. Flash chromatography was carried out using prepacked Teledyne Isco Redisep™ Rf silica-gel columns as the stationary phase and analytical grade solvents as the eluent unless otherwise stated. ¹H nuclear magnetic resonance (NMR) spectra were recorded on an Avance™ 301 Bruker instrument operating at 300.13 MHz and 400.37 MHz at ambient temperature. Chemical shifts are reported in parts per million (δ) and coupling constants in Hz. ¹H NMR spectra were referenced to the residual solvent peaks as internal standards (7.26 ppm for CDCl₃, 2.50 ppm for DMSO-d₆, and 3.34 ppm for CD₃OD). Spin multiplicities are described as s (singlet), brs (broad singlet), d (doublet), t (triplet), q (quartet) and m (multiplet). Total ion current traces were obtained for electrospray positive and negative ionization (ES+/ES−) on a Bruker Esquire Liquid Chromatograph-Ion trap mass spectrometer. Purity of all final compounds were reported >95% pure and judged by high-performance liquid chromatography (HPLC) using Atlantis DC18 (250×46) nm, Phenomenex Gemini C18 (250×46) nm and X-Bridge (50×46) nm column and method (mobile phase A: 0.1 TFA in water and mobile phase B: acetonitrile) and (mobile phase A: 10 nm NH4OAc in milli water: mobile phase B: acetonitrile). Analytical grade solvents as the eluent were used unless otherwise stated. Chiral purification was carried out by supercritical fluid chromatography (SFC) using prepacked Lux A1 column and Chiralcel-OD-H column and analytical grade solvents were used as the eluent unless otherwise stated.

Example 1: Synthesis of Compounds According to the Invention

The compounds of the invention can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

Compounds 1 to 36 of the invention are synthesized as described in the general synthetic routes described herein. In particular, for Compounds of Formula (I) when both R₂ are joined to form an optionally substituted cyclopropyl, compounds are synthesized according to Scheme 3 below.

Scheme 3

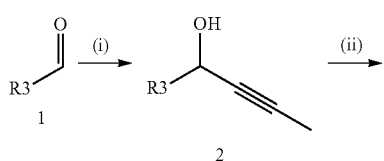

-continued

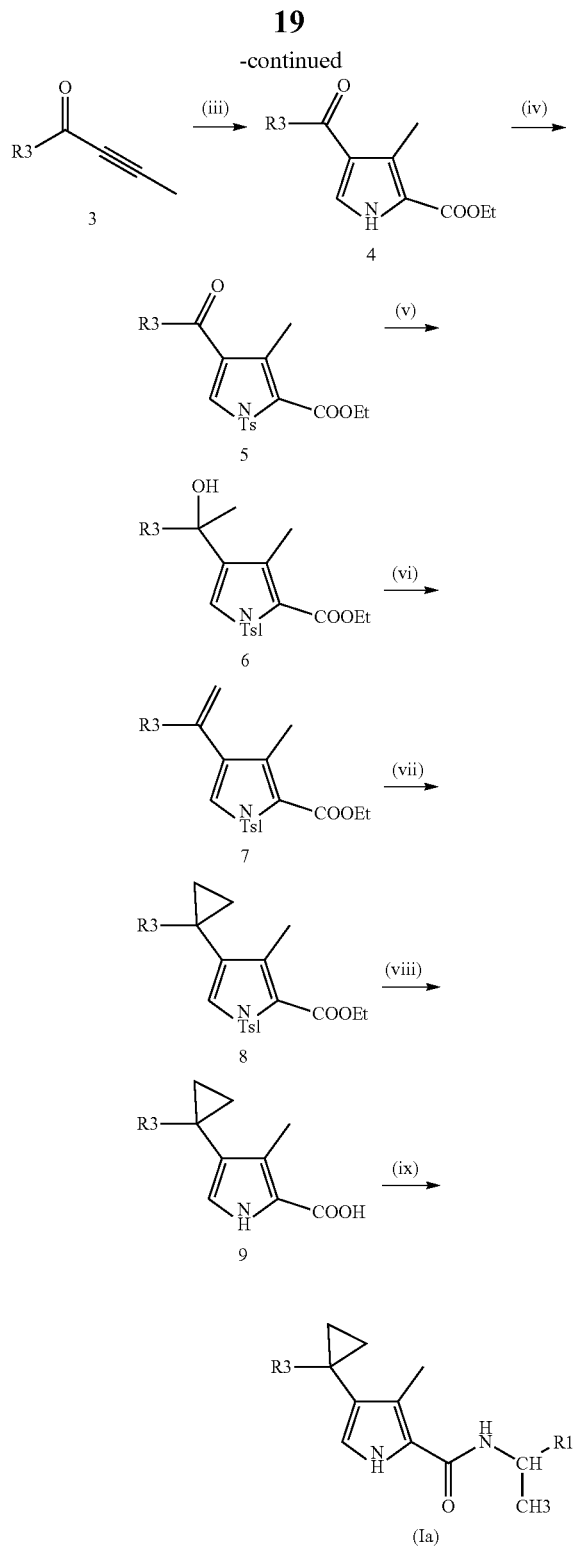

Reagents and Conditions: (i) 1-Propynylmagnesium bromide, THF, 0° C.-RT, 2-6 h (ii) Dess-Martin, CH₂Cl₂, RT, 2-4 h (iii) Ethyl isocyanoacetate, Ag₂CO₃, NMP, 80° C., 3-6 h (iv) NaH, TsCl, DMF, 0° C.-RT (v) MeMgBr, THF, 0° C.-RT (vi) Iodine (catalytic), toluene, 115° C., 16 h (vii) Trimethylsulfoxoniumiodide, t-BuOK, THF (viii) NaOH, EtOH:H₂O, 80° C., 2 h (ix) Amine, HATU, Et₃N, CH₂Cl₂, 4-8 h.

Preparation of 3-methyl-N-(1-(1H-1,2,4-triazol-3-yl) ethyl)-4-(1-(6-(trifluoromethyl) pyridin-3-yl)cyclopropyl)-1H-pyrrole-2-carboxamide (Compound 1)

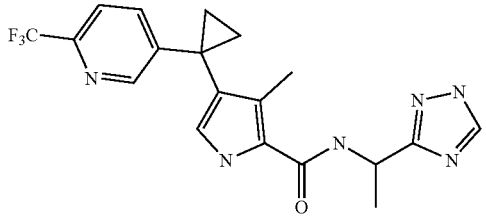 [SMILES: Cc1c(C2(c3ccc(C(F)(F)F)nc3)CC2)c[nH]c1C(=O)NC(C)c1nc[nH]n1]

The synthesis of the title compound was carried out as described in Scheme 1 using intermediates 1a-9a.

Step (i)

1-Propynylmagnesium bromide (0.5 M in THF) (127 mL, 63.22 mmol) was added to 6-(trifluoromethyl)pyridine-3-carbaldehyde (intermediate 1a) (10 g, 57.47 mmol) in THF (150 mL) at 0° C. and stirred for 4 h at RT. Reaction mixture was quenched with 1.5 N HCl solution and extracted with ethyl acetate (2×30 mL). The resulting organic layer was washed with brine, dried over Na₂SO₄ and concentrated to afford 1-(6-(trifluoromethyl)pyridin-3-yl)but-2-yn-1-ol (2a) (11.2 g, 94%) as a colorless liquid. $^1$H NMR (400 MHz, DMSO-d₆) δ (ppm): 8.96 (s, 1H), 8.26-8.31 (m, 1H), 8.02 (d, 1H, J=8.1 Hz), 3.57 (s, 3H); ESIMS m/z (M+1):216.0.

Step (ii)

Dess-Martin (32.5 g, 76.74 mmol) was added to stirred solution of intermediate (2a) (11.0 g, 51.1 mmol) in CH₂Cl₂ (150 mL) at RT and continued for 2 h. The reaction mixture was quenched with saturated sodium bicarbonate solution, extracted with CH₂Cl₂. The combined organic layers were dried (Na₂SO₄), filtered and concentrated. The concentrated product was purified by flash chromatography (silica gel, eluting with hexane:EtOAc mixtures from 100% to 80:20%) to afford the title compound 1-(6-(trifluoromethyl)pyridin-3-yl)but-2-yn-1-one (3a) (9.0 g, 83%) as an off white solid. $^1$H NMR (300 MHz, DMSO-d₆) δ (ppm): 10.21 (s, 1H), 8.66 (d, 1H, J=8.2 Hz), 8.14 (d, 1H, J=8.2 Hz), 2.21 (s, 3H). ESIMS m/z (M+1): 214.2.

Step (iii)

Intermediate (3a) (9.0 g, 42.20 mmol) was added to stirred solution of silver carbonate (1.20 g, 4.22 mmol) in NMP (100 mL) at RT. Ethyl isocyanoacetate (7.20 g, 63.3 mmol) was added at room temperature and stirred for 2 h at 80° C. Reaction mixture was cooled to RT, quenched with water (800 mL), and extracted with ethyl acetate (2×400 mL). The combined organic layers were dried (Na₂SO₄), filtered and concentrated. The concentrated product was purified by flash chromatography (silica gel, eluting with hexane: EtOAc mixtures from 100% to 60:40%) to afford the title compound ethyl 3-methyl-4-(6-(trifluoromethyl)pyridine-3-carbonyl)-1H-pyrrole-2-carboxylate (4a) (6 g, 44%) as an off white solid. $^1$H NMR (300 MHz, DMSO-d₆) δ(ppm): 12.43 (s, 1H), 9.00 (s, 1H), 8.33 (d, 1H, J=8.1 Hz), 8.05 (d, 1H, J=8.1 Hz), 7.45 (s, 1H), 4.30 (q, 2H, J=7.1 Hz), 2.51 (s, 3H), 1.31 (t, 3H, J=7.1 Hz); ESIMS m/z (M+1): 327.2.

Step (iv)

Sodium hydride (0.35 g, 36.78 mmol) was added to a stirred solution of intermediate (4a) (2.5 g, 7.66 mmol) in DMF (20 mL) at 0° C. for 30 min. TsCl (1.4 g, 7.66 mmol) was added at RT and the reaction mixture was stirred at same temperature for 4 h. Water (100 mL) was added to reaction mixture and extracted with ethyl acetate (2×100 mL). The resulting combined organic layer was washed with brine, dried over $Na_2SO_4$ and concentrated. The concentrated product was purified by flash chromatography (silica gel, eluting with hexane:EtOAc mixtures from 100% to 60:40%) to afford ethyl 3-methyl-1-(4-methylbenzenesulfonyl)-4-(6-(trifluoromethyl)pyridine-3-carbonyl)-1H-pyrrole-2-carboxylate (5a) (2.0 g, 55%). $^1$H NMR (300 MHz, DMSO-$d_6$) δ(ppm): 9.12 (s, 1H), 8.45 (d, 1H, J=8.1 Hz), 8.23 (s, 1H), 8.13 (d, 1H, J=8.1 Hz), 7.98 (d, 2H, J=8.4 Hz), 7.50 (d, 2H, J=8.4 Hz), 4.25 (q, 2H, J=7.2 Hz), 2,43 (s, 3H), 2.40 (s, 3H), 1.22 (t, 3H, J=7.2 Hz); ESIMS m/z (M+1): 480.9.

Step (v)

Methyl magnesium bromide (2.0 M in THF) (2.50 mL, 4.99 mmol) was added to intermediate (5a) (2.0 g, 4.17 mmol) in THF (20 mL) at 0° C. and stirred for 4 h at RT. Reaction mixture was quenched with 1.5 N HCl solution and extracted with ethyl acetate (2×50 mL). The resulting organic layer was washed with brine, dried over $Na_2SO_4$ and concentrated to afford ethyl 4-(1-hydroxy-1-(6-(trifluoromethyl)pyridin-3-yl)ethyl)-3-methyl-1-(4-methylbenzenesulfonyl)-1H-pyrrole-2-carboxylate (6a) (1.5 g) as a colorless liquid. ESIMS m/z (M+1): 497.2. The product was taken for the next step without purification.

Step (vi)

Iodine (100 mg, catalytic amount) was added to intermediate (6a) (1.5 g, 3.02 mmol) in toluene (20 mL) at RT and stirred for 16 h at 115° C. Reaction mixture was quenched with 10% $Na_2S_2O_3$ solution and extracted with ethyl acetate (2×50 mL). The resulting organic layer was washed with brine, dried over $Na_2SO_4$ and concentrated to afford ethyl 3-methyl-1-(4-methylbenzenesulfonyl)-4-(1-(6-(trifluoromethyl)pyridin-3-yl)ethenyl)-1H-pyrrole-2-carboxylate (7a) (1.5 g, 76%) as grey solid. $^1$H NMR (400 MHz, DMSO-d6) δ(ppm): 8.79 (s, 1H), 7.88-7.95 (m, 4H), 7.75 (s, 1H), 7.49 (d, 2H, J=8.2 Hz), 5.99 (s, 1H), 5.66 (s, 1H), 4.19 (q, 2H, J=7.1 Hz), 2.43 (s, 3H), 1.88 (s, 3H), 1.19 (t, 3H, J=7.1 Hz); ESIMS m/z (M+1): 480.0.

Step (vii)

A solution of intermediate (7a) (1.1 g, 2.09 mmol) in THF (10 mL) was added to a stirred solution of trimethylsulfoxonium iodide (0.85 g, 4.18 mmol) and t-BuOK (0.47 g, 4.18 mmol) in DMSO (3 mL) at 0° C. and stirred for 4 h at RT. Reaction mixture was poured in to water (20 mL) and extracted with ethyl acetate (2×50 mL). The combined organic layers were dried ($Na_2SO_4$), filtered and concentrated. The concentrated product was purified by flash chromatography (silica gel, eluting with hexane:EtOAc mixtures from 100% to 60:40%) to afford ethyl 3-methyl-1-(4-methylbenzenesulfonyl)-4-(1-(6-(trifluoromethyl)pyridin-3-yl) cyclopropyl)-1H-pyrrole-2-carboxylate (8a) (0.8 g, 71%) as off white solid. $^1$H NMR (400 MHz, DMSO-$d_6$) δ (ppm): 8.41 (s, 1H), 7.89 (d, 2H, J=8.3 Hz), 7.80 (s, 1H), 7.77 (d, 1H, J=8.3 Hz), 7.67-7.69 (m, 1H), 7.48 (d, 2H, J=8.1 Hz), 4.16 (q, 2H, J=7.1 Hz), 2.42 (s, 3H), 1.96 (s, 3H), 1.44-1.47 (m, 2H), 1.37-1.40 (m, 2H), 1.17 (t, 3H, J=7.1 Hz); ESIMS m/z (M+1): 494.1.

Step (viii)

Sodium hydroxide (0.2 g, 4.87 mmol) was added to a stirred solution of intermediate (8a) (0.8 g, 1.62 mmol) in EtOH:water (8:2 mL) at RT and heated to 80° C. for 2 h. The resulting reaction mixture was concentrated and quenched with water (10 mL). Then, it was acidified with 10% citric acid solution. The solid obtained was filtered, washed with water and dried to afford 3-methyl-4-(1-(6-(trifluoromethyl) pyridin-3-yl)cyclopropyl)-1H-pyrrole-2-carboxylic acid (9a, 0.45 g, 89%) as an off white solid. $^1$H NMR (400 MHz, DMSO-$d_6$) δ (ppm): 11.36 (s, 1H), 8.40 (s, 1H), 7.74 (d, 1H, J=8.4 Hz), 7.63 (d, 1H, J=8.4 Hz), 6.91 (s, 1H), 2.09 (s, 3H), 1.40 (brs, 2H), 1.28 (brs, 2H); ESIMS m/z: 311.2; LCMS: 98.02%; HPLC purity: 94.73%.

Step (ix)

1-(1-(Triphenylmethyl)-1H-1, 2, 4-triazol-3-yl)ethan-1-amine (0.21 g, 0.58 mmol) and triethylamine (0.13 mL, 0.96 mmol) were added to a stirred solution of intermediate (9a) (0.15 g, 0.48 mmol) in dichloromethane (6 mL) at RT and continued stirring for 5 min. Then, HATU (0.27 g, 0.72 mmol) was added to the reaction mixture and stirred at same temperature for 4 h. After completion of reaction (monitored by TLC), water was added to reaction mixture and extracted with dichloromethane (2×10 mL). The combined organic layer was dried over $Na_2SO_4$ and concentrated. The resulting concentrated product was purified by column chromatography using 10-50% ethyl acetate in petroleum ether to afford 3-methyl-4-(1-(6-(trifluoromethyl)pyridin-3-yl)cyclopropyl)-N-(1-(1-(triphenylmethyl)-1H-1,2,4-triazol-3-yl) ethyl)-1H-pyrrole-2-carboxamide (180 mg, 54%) as white solid. Product was taken into the next step without purification.

To a stirred solution of 3-methyl-4-(1-(6-(trifluoromethyl) pyridin-3-yl)cyclopropyl)-N-(1-(1-(triphenylmethyl)-1H-1, 2,4-triazol-3-yl)ethyl)-1H-pyrrole-2-carboxamide (180 mg, 0.28 mmol) in TFA (0.72 mL, 4 vol) and $CH_2Cl_2$ (1 mL), was added triethylsilane (0.36 mL, 2 vol) at RT and continued for 1 h. After completion of reaction, reaction mixture was quenched with saturated $NaHCO_3$ (5 mL) by dropwise addition at 0° C. and extracted with dichloromethane (3×10 mL). The combined organic layers were dried ($Na_2SO_4$), filtered and concentrated. The resulting concentrated product was purified by column chromatography using 0-5% methanol in dichloromethane to afford 3-methyl-N-(1-(1H-1,2,4-triazol-3-yl)ethyl)-4-(1-(6-(trifluoromethyl)pyridin-3-yl)cyclopropyl)-1H-pyrrole-2-carboxamide (Compound 1, 90 mg, 80%) as an off white solid. $^1$H NMR (400 MHz, $CD_3OD$) δ (ppm): 8.36 (s, 2H), 7.68 (s, 2H), 6.93 (s, 1H), 5.38 (q, 1H, J=6.8 Hz), 2.21 (s, 3H), 1.63 (d, 3H, J=6.8 Hz), 1.42-1.45 (m, 2H), 1.36-1.39 (m, 2H); ESIMS m/z: 405.1; LCMS: 94.70%; HPLC purity: 94.72%.

Compounds 2 and 3 (Enantiomers)

Racemic Compound 1 was separated by SFC purification to afford 3-methyl-N-[1-(1H-1,2,4-triazol-3-yl)ethyl]-4-{1-[6-(trifluoromethyl)pyridin-3-yl]cyclopropyl}-1H-pyrrole-2-carboxamide, enantiomer I (Compound 2, 21 mg; retention time: 2.07) as off white solid; $^1$H NMR (400 MHz, $CD_3OD$) δ (ppm): 8.36 (s, 2H), 7.68 (s, 2H), 6.93 (s, 1H), 5.38 (q, 1H, J=6.8 Hz), 2.21 (s, 3H), 1.63 (d, 3H, J=6.8 Hz), 1.42-1.45 (m, 2H), 1.36-1.39 (m, 2H); ESIMS m/z (M+1): 405.2; HPLC purity: 99.36%; SFC purity 100% and 3-Methyl-N-[1-(1H-1,2,4-triazol-3-yl)ethyl]-4-{1-[6-(trifluoromethyl)pyridin-3-yl]cyclo-propyl}-1H-pyrrole-2-carboxamide, enantiomer II (Compound 3; 18 mg; retention time: 3.81) as off white solid; $^1$H NMR (400 MHz, $CD_3OD$) δ (ppm): 8.36 (s, 2H), 7.68 (s, 2H), 6.93 (s, 1H), 5.38 (q, 1H, J=6.8 Hz), 2.21 (s, 3H), 1.63 (d, 3H, J=6.8 Hz), 1.42-1.45 (m, 2H), 1.36-1.39 (m, 2H); ESIMS m/z: 405.2; HPLC purity: 98.47%; SFC purity 100%.

Preparation of N-(1-(1H-1,2,4-triazol-3-yl)ethyl)-4-(3-fluoro-4-(trifluoromethyl)benzyl)-3-methyl-1H-pyrrole-2-carboxamide (Compound 4)

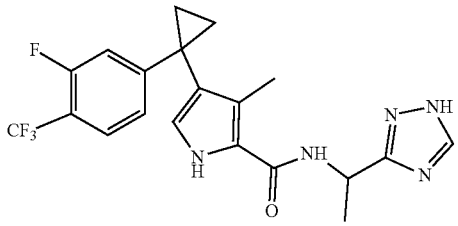 [SMILES: Cc1c(C2(c3ccc(C(F)(F)F)c(F)c3)CC2)c[nH]c1C(=O)NC(C)c1nc[nH]n1]

Compound 4 was synthesised by an analogous method to Scheme 3 using intermediate 3b below as intermediate 3.

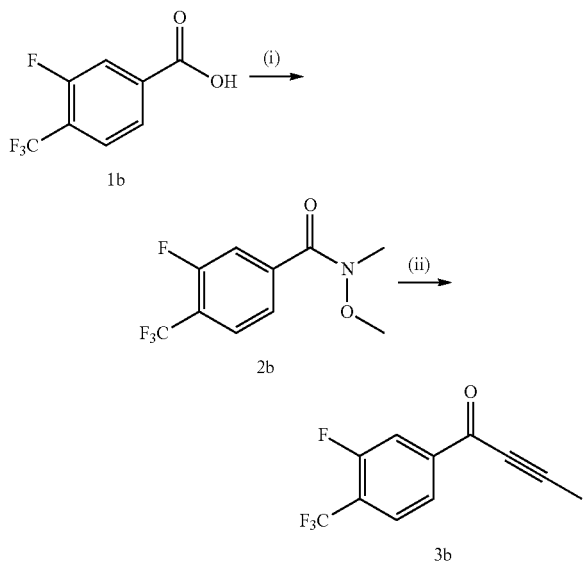

Reagent and conditions: (i) 1'-Carbonyldiimidazole, N,O-dimethyl hydroxylamine hydrochloride, DMF, 4 h (ii) 1-Propynylmagnesium bromide, THF, 0° C. to RT, 2 h.

Step (i, ii) 1,1'-Carbonyldiimidazole (46.7 g, 288.30 mmol) was added to a stirred solution of 3-fluoro-4-(trifluoromethyl)benzoic acid (1b) (50.0 g, 240.20 mmol) in DMF (500 mL) at RT for 1 h. Then, N, O-dimethyl hydroxylamine hydrochloride (27.82 g, 288.3 mmol) was added to the reaction mixture at RT and continued stirring for 4 h. Completion of the reaction was confirmed by UPLC. The reaction mixture was poured into water and extracted with ethyl acetate (2×800 mL). The combined organic layers were dried ($Na_2SO_4$), filtered and concentrated. The concentrated product was purified by flash chromatography (silica gel, eluting with hexane:EtOAc mixtures from 100% to 70:30%) to afford 3-fluoro-N-methoxy-N-methyl-4-(trifluoromethyl)benzamide (2b) (39.2 g, 65%) as yellow liquid. $^1$H NMR (400 MHz, DMSO-$d_6$) δ (ppm): 7.84-7.88 (m, 1H), 7.64 (d, 1H, J=11.2 Hz), 7.56 (d, 1H, J=8.0 Hz), 3.52 (s, 3H), 3.26 (s, 3H); ESIMS m/z (M+1): 252.2.

1-Propynylmagnesium bromide (0.5 M in THF) (375 mL, 187.30 mmol) was added to intermediate (2b) (39.2 g, 156.30 mmol) in THF (300 mL) at 0° C. and stirred for 2 h at RT. Reaction mixture was quenched with 1.5 N HCl solution and extracted with ethyl acetate (2×600 mL). The resulting organic layer was washed with brine, dried over $Na_2SO_4$ and concentrated to afford 1-(3-fluoro-4-(trifluoromethyl)phenyl)but-2-yn-1-one (3b) 32.5 g, 90%) as yellow liquid. $^1$H NMR (400 MHz, DMSO-$d_6$) δ (ppm): 8.01-8.10 (m, 3H), 2.26 (s, 3H); ESIMS m/z (M+1): 230.9.

Step (iii)
Intermediate (3b) (32.5 g, 141.21 mmol) was added to stirred solution of silver carbonate (7.78 g, 28.20 mmol) in NMP (200 mL) at RT. Ethyl isocyanoacetate (23.9 g, 211.80 mmol) was added at room temperature and stirred for 2 h at 80° C. Reaction mixture was cooled to RT, quenched with water (800 mL), and extracted with ethyl acetate (2×600 mL). The combined organic layers were dried ($Na_2SO_4$), filtered and concentrated. The concentrated product was purified by flash chromatography (silica gel, eluting with hexane:EtOAc mixtures from 100% to 60:40%) to afford the title compound ethyl 4-(3-fluoro-4-(trifluoromethyl)benzoyl)-3-methyl-1H-pyrrole-2-carboxylate (4b) (24.5 g, 51%) as an off white solid. $^1$H NMR (400 MHz, DMSO-$d_6$) δ (ppm): 12.38 (brs, 1H), 7.90-7.95 (m, 1H), 7.66-7.77 (m, 2H), 7.40 (d, 1H, J=4.8 Hz), 4.29 (q, 2H, J=7.2 Hz), 2.58 (s, 3H), 1.33 (t, 3H, J=7.2 Hz); ESIMS m/z (M−1): 342.2.

Step (iv)
Sodium hydride (4.28 g, 107.10 mmol) was added to a stirred solution of intermediate (4b) (24.5 g, 71.37 mmol) in DMF (200 mL) at 0° C. for 30 min. TsCl (20.41 g, 107.1 mmol) was added at 0° C. and stirred for 4 h at room temperature. Ice cold water (800 mL) was added to reaction mixture and extracted with ethyl acetate (2×600 mL). The resulting combined organic layer was washed with brine, dried over $Na_2SO_4$ and concentrated. The concentrated product was purified by flash chromatography (silica gel, eluting with hexane:EtOAc mixtures from 100% to 80:20%) to afford ethyl 4-(3-fluoro-4-(trifluoromethyl)benzoyl)-3-methyl-1-(4-methylbenzene-1-sulfonyl)-1H-pyrrole-2-carboxylate (5b) (27.4 g, 78%). $^1$H NMR (400 MHz, DMSO-$d_6$) δ (ppm): 8.16 (s, 1H), 7.92-8.09 (m, 3H), 7.79-7.90 (m, 2H), 7.49-7.51 (m, 2H), 4.24 (q, 2H, J=9.2 Hz), 2.43 (s, 3H), 2.38 (s, 3H), 1.22 (t, 3H, J=9.2 Hz); ESIMS m/z (M−1): 496.2.

Step (v)
Methyl magnesium bromide (1.0 M in THF) (66 mL, 66.10 mmol) was added to intermediate (5b) (27.4 g, 55.10 mmol) in THF (250 mL) at 0° C. and stirred for 2 h at RT. Reaction mixture was quenched with 1.5 N HCl solution and extracted with ethyl acetate (2×600 mL). The resulting organic layer was washed with brine, dried over $Na_2SO_4$ and concentrated to afford ethyl 4-(1-(3-fluoro-4-(trifluoromethyl)phenyl)-1-hydroxyethyl)-3-methyl-1-(4-methylbenzene-1-sulfonyl)-1H-pyrrole-2-carboxylate (6b) (19.1 g, 68%) as colorless liquid. 1H NMR (400 MHz, DMSO-$d_6$) δ (ppm): 7.90-7.93 (m, 2H), 7.68-7.75 (m, 2H), 7.49-7.51 (m, 2H), 7.37-7.41 (m, 1H), 7.28-7.30 (m, 1H), 6.06 (s, 1H), 4.14 (q, 2H, J=9.6 Hz), 2.42 (s, 3H), 1.76 (s, 3H), 1.70 (s, 3H), 1.13 (t, 3H, J=9.6 Hz); ESIMS m/z (M+1): 514.0.

Step (vi)
Iodine (18.8 g, 74.40 mmol) was added to intermediate (6b) (19.1 g, 37.20 mmol) in toluene (200 mL) at RT and stirred for 16 h at 115° C. Reaction mixture was quenched with 10% $Na_2S_2O_3$ solution and extracted with ethyl acetate (2×600 mL). The resulting organic layer was washed with brine, dried over $Na_2SO_4$ and concentrated. The concentrated product was purified by flash chromatography (silica gel, eluting with hexane:EtOAc from 100% to 90:10%) to afford ethyl 4-(1-(3-fluoro-4-(trifluoromethyl)phenyl)ethenyl)-3-methyl-1-(4-methylbenzene-1-sulfonyl)-1H-pyrrole- 2-carboxylate (7b) (17.2 g, 93%) as grey solid. $^1$H NMR (400 MHz, DMSO-d$_6$) δ (ppm): 7.90-7.92 (m, 2H), 7.72-7.79 (m, 2H), 7.47-7.51 (m, 3H), 7.26 (d, 1H, J=10.8 Hz), 5.96 (s, 1H), 5.59 (s, 1H), 4.20 (q, 2H, J=9.6 Hz), 2.42 (s, 3H), 1.84 (s, 3H), 1.18 (t, 3H, J=9.6 Hz); ESIMS m/z (M+1): 496.2.

Step (vii)

To stirred solution of intermediate (7b) (17.2 g, 34.70 mmol) in THF (60 mL) was added to a stirred solution of trimethylsulfoxonium iodide (15.3 g, 69.40 mmol) and $^t$BuOK (7.79 g, 69.40 mmol) in DMSO (30 mL) at 0° C. and stirred for 4 h at RT. Reaction mixture was poured in to water (200 mL) and extracted with ethyl acetate (2×500 mL). The combined organic layers were dried (Na$_2$SO$_4$), filtered and concentrated. The concentrated product was purified by flash chromatography (silica gel, eluting with hexane:EtOAc mixtures from 100% to 60:40%) to afford ethyl 4-(1-(3-fluoro-4-(trifluoromethyl)phenyl)cyclopropyl)-3-methyl-1-(4-methylbenzene-1-sulfonyl)-1H-pyrrole-2-carboxylate (8b) (11.2 g, 63%) as off white solid. 1H NMR (400 MHz, DMSO-d$_6$) δ (ppm): 7.86-7.89 (m, 2H), 7.75 (s, 1H), 7.59-7.62 (m, 1H), 7.46-7.49 (m, 2H), 6.96-7.08 (m, 2H), 4.16 (q, 2H, J=9.6 Hz), 2.28 (s, 3H), 1.36-1.39 (m, 4H), 1.84 (s, 3H), 1.18 (t, 3H, J=9.2 Hz); ESIMS m/z (M+1): 510.0.

Step (viii)

Sodium hydroxide (1.75 g, 43.96 mmol) was added to a stirred solution of intermediate (8b) (11.2 g, 22.00 mmol) in EtOH:water (80:20 mL) at RT and heated to 80° C. for 2 h. The resulting reaction mixture was concentrated and quenched with water (100 mL). Then, it was acidified with 10% citric acid solution. The solid obtained was filtered, washed with water and dried to afford 4-(3-fluoro-4-(trifluoromethyl)benzyl)-3-methyl-1H-pyrrole-2-carboxylic acid (9b) (6 g, 84%) as an off white solid. $^1$H NMR (400 MHz, DMSO-d$_6$) δ (ppm): 11.04 (brs, 1H), 7.57-7.61 (m, 1H), 6.98-7.03 (m, 2H), 6.74 (s, 1H), 2.08 (s, 3H), 1.30-1.32 (m, 2H), 1.22-1.24 (m, 2H); ESIMS m/z (M−1): 326.1.

Step (ix)

1-(1-Triphenylmethyl-1H-1, 2, 4-triazol-3-yl)ethan-1-amine (6.5 g, 18.30 mmol) and triethylamine (4.8 mL, 36.70 mmol) were added to a stirred solution of intermediate (9b) (6 g, 18.40 mmol) in dichloromethane (60 mL) at RT and continued stirring for 5 min. Then, HATU (10.5 g, 27.50 mmol) was added to the reaction mixture and stirred at same temperature for 5 h. After completion of reaction (monitored by TLC), water was added to reaction mixture and extracted with dichloromethane (2×400 mL). The combined organic layer was dried over Na$_2$SO$_4$ and concentrated. The resulting concentrated product was purified by column chromatography using 10-50% ethyl acetate in petroleum ether to afford 4-(3-fluoro-4-(trifluoromethyl)benzyl)-3-methyl-N-(1-(1-triphenylmethyl-1H-1,2,4-triazol-3-yl)ethyl)-1H-pyrrole-2-carboxamide (8.5 g, 69%) as gummy solid. To a stirred solution of 4-(3-fluoro-4-(trifluoromethyl)benzyl)-3-methyl-N-(1-(1-triphenylmethyl-1H-1,2,4-triazol-3-yl) ethyl)-1H-pyrrole-2-carboxamide (8.5 g, 12.80 mmol) in TFA (80 mL, 4 vol) and CH$_2$Cl$_2$ (25 mL) was added triethylsilane (40 mL, 2 vol) at RT and continued for 1 h. After completion of reaction, reaction mixture was quenched with saturated NaHCO$_3$ (100 mL) by dropwise addition at 0° C. and extracted with dichloromethane (3×200 mL). The combined organic layers were dried (Na$_2$SO$_4$), filtered and concentrated. The resulting concentrated product was purified by column chromatography using 0-5% methanol in dichloromethane to afford N-(1-(1H-1,2,4-triazol-3-yl)ethyl)-4-(3-fluoro-4-(trifluoromethyl)benzyl)-3-methyl-1H-pyrrole-2-carboxamide (Compound 4; 3 g, 55.6%) as an off white solid. $^1$H NMR (400 MHz, DMSO-d$_6$) δ (ppm): 13.82 (s, 1H), 11.16 (brs, 1H), 8.49 (brs, 1H), 7.67-7.86 (m, 1H), 7.57-7.61 (m, 1H), 6.97-7.04 (m, 2H), 6.88 (brs, 1H), 5.24 (brs, 1H), 2.10 (s, 3H), 1.49 (brs, 3H), 1.35 (m, 2H), 1.24 (m, 2H); ESIMS m/z (M+1): 422.1; LCMS: 95.83%; HPLC purity: 95.21%.

Compounds 5 and 6 (Enantiomers)

Racemic Compound 4 was separated by SFC to afford N-(1-(1H-1,2,4-triazol-3-yl) ethyl)-4-(3-fluoro-4-(trifluoromethyl)benzyl)-3-methyl-1H-pyrrole-2-carboxamide enantiomer I (Compound 5; 17 mg; retention time: 1.48) as an off white solid. $^1$H NMR (400 MHz, CD$_3$OD) δ (ppm): 8.47 (brs, 1H), 7.48-7.57 (m, 1H), 6.99 (d, 1H), 6.89-6.95 (m, 2H), 5.38 (brs, 1H), 2.20 (s, 3H), 1.59-1.63 (brs, 3H), 1.31-1.42 (m, 4H); ESIMS m/z (M+1): 422.1; LCMS: 98.08%; HPLC purity: 92.20%; SFC purity 96.07% and N-(1-(1H-1,2,4-triazol-3-yl)ethyl)-4-(3-fluoro-4-(trifluoromethyl)benzyl)-3-methyl-1H-pyrrole-2-carboxamide enantiomer II (Compound 6; 20 mg; retention time: 2.45) as an off white solid. $^1$H NMR (400 MHz, CD$_3$OD) δ (ppm): 8.46 (brs, 1H), 7.48-7.53 (t, 1H), 6.99 (d, 1H), 6.90-6.95 (m, 2H), 5.38 (brs, 1H), 2.20 (s, 3H), 1.59-1.64 (brs, 3H), 1.31-1.42 (m, 4H); ESIMS m/z (M+1): 422.1; LCMS: 98.53%; HPLC purity: 90.95%; SFC purity 97.84%.

Preparation of N-(1-(1H-pyrazol-4-yl)ethyl)-3-methyl-4-(1-(6-(trifluoromethyl)pyridin-3-yl)cyclopropyl)-1H-pyrrole-2-carboxamide (Compound 7)

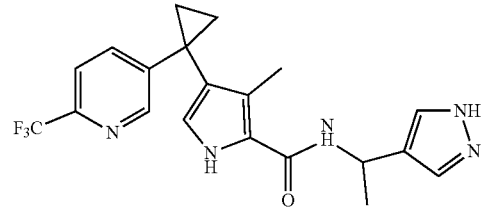 [SMILES: Cc1c(C2(c3ccc(C(F)(F)F)nc3)CC2)c[nH]c1C(=O)NC(C)c1cn[nH]c1]

Compound 7 was synthesised by an analogous method to Scheme 3.

1-(1-(Triphenylmethyl)-1H-pyrazol-4-yl)ethan-1-amine (0.28 g, 0.77 mmol) and triethylamine (0.2 mL, 1.30 mmol) were added to a stirred solution of 3-methyl-4-(1-(6-(trifluoromethyl)pyridin-3-yl)cyclopropyl)-1H-pyrrole-2-carboxylic acid (9a) (200 mg, 0.65 mmol) in dichloromethane (4 mL) at RT and continued stirring for 5 min. Then, HATU (0.37 g, 3.16 mmol) was added to the reaction mixture and stirred at same temperature for 4 h. After completion of reaction (monitored by TLC), water was added to reaction mixture and extracted with dichloromethane (2×50 mL). The combined organic layer was dried over Na$_2$SO$_4$ and concentrated. The resulting concentrated product was purified by column chromatography using 10-50% ethyl acetate in petroleum ether to afford 3-methyl-4-(1-(6-(trifluoromethyl) pyridin-3-yl)cyclopropyl)-N-(1-(1-trityl-1H-pyrazol-4-yl) ethyl)-1H-pyrrole-2-carboxamide (140 mg, 34%) as gummy solid. The solid compound was taken for the next step without purification.

To a stirred solution of 3-methyl-4-(1-(6-(trifluoromethyl) pyridin-3-yl)cyclopropyl)-N-(1-(1-trityl-1H-pyrazol-4-yl) ethyl)-1H-pyrrole-2-carboxamide (0.14 g, 0.22 mmol) in TFA (0.6 mL, 4 vol) was added triethylsilane (0.3 mL, 2 vol) at RT and stirred for 1 h. The reaction mixture was quenched with saturated NaHCO$_3$ (20 mL) by dropwise addition at 0°

C. and extracted with dichloromethane (3×50 mL). The combined organic layers were dried (Na₂SO₄), filtered and concentrated. The resulting concentrated product was purified by column chromatography using 0-5% methanol in dichloromethane to afford N-(1-(1H-pyrazol-4-yl)ethyl)-3-methyl-4-(1-(6-(trifluoromethyl)pyridin-3-yl)cyclopropyl)-1H-pyrrole-2-carboxamide (Compound 7; 60 mg, 71%) as off white solid. ¹H NMR (400 MHz, DMSO-d₆) δ (ppm): 11.07 (s, 1H), 8.39 (s, 1H), 7.72 (d, 1H, J=8.0 Hz), 7.64 (s, 1H), 7.62 (brs, 1H), 7.51 (d, 1H, J=8.0 Hz), 7.45 (brs, 1H), 6.87 (s, 1H), 5.05-5.11 (m, 1H), 2.09 (s, 3H), 1.39-1.43 (m, 4H), 1.24 (brs, 3H). ESIMS m/z (M+1): 404.2; LCMS: 89.23%; HPLC purity: 96.41%.

Compounds 8 and 9 (Enantiomers)

The racemic Compound 7 was separated by SFC purification to afford N-(1-(1H-pyrazol-4-yl)ethyl)-3-methyl-4-(1-(6-(trifluoromethyl)pyridin-3-yl)cyclopropyl)-1H-pyrrole-2-carboxamide, enantiomer I (Compound 8; 18 mg; retention time: 2.41), ¹H NMR (400 MHz, DMSO-d₆) δ (ppm): 11.07 (s, 1H), 8.39 (s, 1H), 7.72 (d, 1H), 7.64 (s, 1H), 7.62 (brs, 1H), 7.51 (d, 1H), 7.45 (brs, 1H), 6.87 (s, 1H), 5.05-5.11 (m, 1H), 2.09 (s, 3H), 1.39-1.43 (m, 4H), 1.24 (brs, 3H). ESIMS m/z: 404.2; HPLC purity 96.93%, SFC purity 98.61%, and N-(1-(1H-pyrazol-4-yl)ethyl)-3-methyl-4-(1-(6-(trifluoromethyl)pyridin-3-yl)cyclopropyl)-1H-pyrrole-2-carboxamide, enantiomer II, (Compound 9; 20 mg; retention time: 3.2), ¹H NMR (400 MHz, DMSO-d₆) δ (ppm): 11.07 (s, 1H), 8.39 (s, 1H), 7.72 (d, 1H), 7.64 (s, 1H), 7.62 (brs, 1H), 7.51 (d, 1H), 7.45 (brs, 1H), 6.87 (s, 1H), 5.05-5.11 (m, 1H), 2.09 (s, 3H), 1.39-1.43 (m, 4H), 1.24 (brs, 3H). ESIMS m/z (M+1): 404.2, HPLC purity 98.54%, SFC purity 96%.

Preparation of 3-methyl-N-[1-(5-methyl-1H-pyrazol-3-yl)ethyl]-4-{1-[6-(trifluoromethyl) pyridine-3-yl]cyclopropyl}-1H-pyrrole-2-carboxamide (Compound 10)

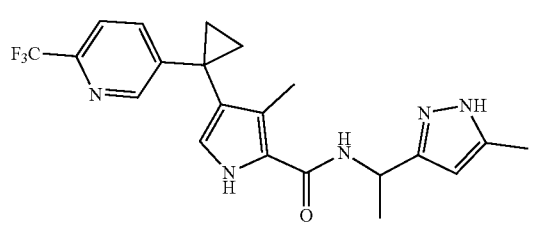 [SMILES: Cc1cc(C(C)NC(=O)c2[nH]cc(C3(c4ccc(C(F)(F)F)nc4)CC3)c2C)n[nH]1]

Compound 10 was synthesised by an analogous method to Scheme 3.

1-(5-Methyl-1H-pyrazol-3-yl)ethan-1-amine (CAS No #1314901-23-9, which can be prepared from ethyl 5-methyl-1H-pyrazole-3-carboxylate (Huang et al., 2017, Journal of Heterocyclic Chemistry, 54, p. 1121-1128)) (45 mg, 0.35 mmol) and triethylamine (0.2 mL, 0.64 mmol) were added to a stirred solution of 3-methyl-4-(1-(6-(trifluoromethyl)pyridin-3-yl)cyclopropyl)-1H-pyrrole-2-carboxylic acid (9a) (100 mg, 0.32 mmol) in dichloromethane (5 mL) at RT and continued for 5 min. Then, HATU (0.18 g, 0.48 mmol) was added to the reaction mixture and stirred at same temperature for 4 h. After completion of reaction (monitored by TLC), water was added to reaction mixture and extracted with dichloromethane (2×40 mL). The combined organic layer was dried over Na₂SO₄ and concentrated. The resulting concentrated product was purified by column chromatography using 10-50% ethyl acetate in petroleum ether to afford 3-methyl-N-[1-(5-methyl-1H-pyrazol-3-yl)ethyl]-4-{1-[6-(trifluoromethyl) pyridine-3-yl]cyclopropyl}-1H-pyrrole-2-carboxamide (Compound 10; 70 mg, 52%) as an off white solid. ¹H NMR (400 MHz, DMSO-d₆) δ (ppm): 12.21 (s, 1H), 11.11 (s, 1H), 8.39 (s, 1H), 7.71 (d, 1H, J=8.3 Hz), 7.62 (d, 1H, J=8.3 Hz), 7.52 (s, 1H), 6.89 (s, 1H), 5.93 (s, 1H), 5.08 (m, 1H), 2.17 (s, 3H), 2.09 (s, 3H), 1.39-1.41 (m, 5H), 1.20-1.25 (m, 2H); ESIMS m/z (M+1): 418.2; LCMS: 97.78%; HPLC purity: 96.80%.

Compounds 11 and 12 (Enantiomers)

The racemic Compound 10 was separated by SFC to afford 3-methyl-N-[1-(5-methyl-1H-pyrazol-3-yl)ethyl]-4-{1-[6-(trifluoromethyl)pyridine-3-yl]cyclopropyl}-1H-pyrrole-2-carboxamide, enantiomer I (Compound 11; 12 mg; retention time: 2.27) as an off white solid; ¹H NMR (400 MHz, DMSO-d₆) δ (ppm): 12.21 (s, 1H), 11.11 (s, 1H), 8.39 (s, 1H), 7.71 (d, 1H, J=8.3 Hz), 7.62 (d, 1H, J=8.3 Hz), 7.52 (s, 1H), 6.89 (s, 1H), 5.93 (s, 1H), 5.09 (m, 1H), 2.17 (s, 3H), 2.09 (s, 3H), 1.39-1.41 (m, 5H), 1.20-1.25 (m, 2H); ESIMS m/z: 418.2; HPLC purity: 98.63%; SFC purity 98.96% and 3-methyl-N-[1-(5-methyl-1H-pyrazol-3-yl)ethyl]-4-{1-[6-(trifluoromethyl)pyridine-3-yl]cyclopropyl}-1H-pyrrole-2-carboxamide, enantiomer II (Compound 12; 17 mg; retention time: 4.07) as an off white solid; ¹H NMR (400 MHz, DMSO-d₆) δ (ppm): 12.21 (s, 1H), 11.14 (s, 1H), 8.39 (s, 1H), 7.71 (d, 1H, J=8.3 Hz), 7.62 (d, 1H, J=8.3 Hz), 7.52 (s, 1H), 6.89 (s, 1H), 5.93 (s, 1H), 5.08 (m, 1H), 2.17 (s, 3H), 2.09 (s, 3H), 1.39-1.41 (m, 5H), 1.20-1.25 (m, 2H); ESIMS m/z: 418.2; HPLC purity: 98.56%; SFC purity 100%.

Preparation of 3-(1-(3-methyl-4-(1-(6-(trifluoromethyl)pyridin-3-yl)cyclopropyl)-1H-pyrrole-2-carboxamido)ethyl)-1H-pyrazole-5-carboxamide (Compound 13)

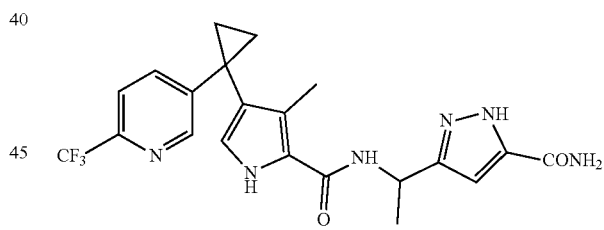

Compound 13 was synthesised by an analogous method to Scheme 3.

Ethyl 3-(1-aminoethyl)-1H-pyrazole-5-carboxylate (0.35 g, 1.94 mmol) and triethylamine (0.5 mL, 3.23 mmol) were added to a stirred solution of compound (9a) (500 mg, 1.62 mmol) in dichloromethane (5 mL) at RT and continued for 5 min. Then, HATU (0.92 g, 2.42 mmol) was added to the reaction mixture and stirred at same temperature for 6 h. After completion of reaction (monitored by TLC), water was added to reaction mixture and extracted with dichloromethane (2×40 mL). The combined organic layer was dried over Na₂SO₄ and concentrated. The resulting concentrated product was purified by column chromatography using 10-80% ethyl acetate in petroleum ether to afford ethyl 3-(1-(3-methyl-4-(1-(6-(trifluoromethyl)pyridin-3-yl)cyclopropyl)-1H-pyrrole-2-carboxamido)ethyl)-1H-pyrazole-5-carboxylate (450 mg, 59%) as gummy solid. The product was used directly without further purification.

Aqueous ammonia (10 ml) was added to a stirred solution of ethyl 3-(1-(3-methyl-4-(1-(6-(trifluoromethyl)pyridin-3-yl)cyclopropyl)-1H-pyrrole-2-carboxamido)ethyl)-1H-pyrazole-5-carboxylate (0.45 g, 0.95 mmol) in methanol (2 mL) and heated to 100° C. for 24 h. The reaction mixture was concentrated and purified by preparative HPLC to afford 3-(1-(3-methyl-4-(1-(6-(trifluoromethyl)pyridin-3-yl)cyclopropyl)-1H-pyrrole-2-carboxamido)ethyl)-1H-pyrazole-5-carboxamide (Compound 13; 150 mg, 36%) as white solid. $^1$H NMR (400 MHz, CD$_3$OD) δ (ppm): 8.35 (s, 1H), 7.67 (s, 2H), 6.91 (s, 1H), 6.71 (s, 1H), 5.34-5.36 (m, 1H), 2.19 (s, 3H), 1.62 (d, 3H), 1.41-1.42 (m, 2H), 1.36-1.37 (m, 2H); ESIMS m/z (M+1): 446.9; LCMS: 99.67%; HPLC purity: 98.46%.

Compounds 14 and 15 (Enantiomers)

The racemic Compound 13 was separated by SFC to afford 3-(1-(3-methyl-4-(1-(6-(trifluoromethyl)pyridin-3-yl)cyclopropyl)-1H-pyrrol-2-yl)formamido)ethyl)-1H-pyrazole-5-carboxamide, enantiomer I (Compound 14; 45 mg; retention time: 2.14) as white solid. 1H NMR (400 MHz, CD$_3$OD) δ (ppm): 8.33 (s, 1H), 7.64 (s, 2H), 6.90 (s, 1H), 6.70 (s, 1H), 5.33-5.34 (m, 1H), 2.17 (s, 3H), 1.60 (d, 3H), 1.39-1.42 (m, 2H), 1.34-1.35 (m, 2H); ESIMS m/z: 447.1; HPLC purity: 98.93%; SFC purity 97.76% and 3-(1-(3-methyl-4-(1-(6-(trifluoromethyl)pyridin-3-yl)cyclopropyl)-1H-pyrrol-2-yl)formamido)ethyl)-1H-pyrazole-5-carboxamide, enantiomer II (Compound 15; 28 mg; retention time: 3.27) as white solid. 1H NMR (400 MHz, CD$_3$OD) δ (ppm): 8.33 (s, 1H), 7.64 (s, 2H), 6.90 (s, 1H), 6.70 (s, 1H), 5.33-5.34 (m, 1H), 2.17 (s, 3H), 1.60 (d, 3H), 1.39-1.42 (m, 2H), 1.34-1.35 (m, 2H); ESIMS m/z: 447.1; HPLC purity: 99.43%; SFC purity 100%.

Preparation of N-(1-(5-cyano-1H-pyrazol-3-yl)ethyl)-3-methyl-4-(1-(6-(trifluoromethyl) pyridin-3-yl)cyclopropyl)-1H-pyrrole-2-carboxamide (Compound 16)

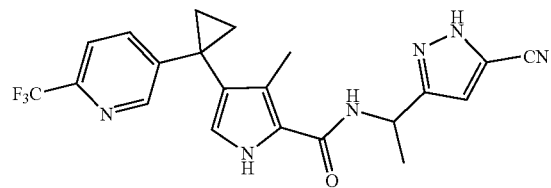 [SMILES: Cc1c(C2(c3ccc(C(F)(F)F)nc3)CC2)c[nH]c1C(=O)NC(C)c1cc(C#N)[nH]n1]

To a stirred solution of Compound 13 (120 mg, 0.27 mmol) in dichloromethane (3 mL) obtained as described above, was added DIPEA (0.25 ml, 1.08 mmol) followed by addition of T$_3$P 50 wt % in ethyl acetate (0.35 mL, 0.54 mmol). The reaction mixture was then stirred for 2 h at RT. After completion of reaction (monitored by TLC), water was added to reaction mixture and extracted with dichloromethane (2×40 mL). The combined organic layer was dried over Na$_2$SO$_4$ and concentrated. The resulting concentrated product was purified by column chromatography using 30-80% ethyl acetate in petroleum ether to afford N-(1-(5-cyano-1H-pyrazol-3-yl)ethyl)-3-methyl-4-(1-(6-(trifluoromethyl)pyridin-3-yl)cyclopropyl)-1H-pyrrole-2-carboxamide (Compound 16; 70 mg, 61%) as an off white solid. $^1$H NMR (400 MHz, DMSO-d$_6$) δ (ppm): 13.86 (s, 1H), 11.08 (s, 1H), 8.40 (s, 1H), 7.83 (d, 1H, J=8.0 Hz), 7.73 (d, 1H, J=8.0 Hz), 7.63-7.65 (m 1H), 6.87 (s, 1H), 6.88 (s, 1H), 5.20-5.24 (m, 1H), 2.05 (s, 3H), 1.48 (d, 3H, J=6.7 Hz), 1.40 (brs, 2H), 1.25 (brs, 2H); ESIMS m/z (M+1): 429.1; LCMS: 98.90%; HPLC purity: 99.27%.

Compounds 17 and 18 (Enantiomers)

The racemic Compound 16 was separated by SFC to afford N-(1-(5-cyano-1H-pyrazol-3-yl)ethyl)-3-methyl-4-(1-(6-(trifluoromethyl)pyridin-3-yl)cyclopropyl)-1H-pyrrole-2-carboxamide, enantiomer I (Compound 17; 12 mg; retention time: 2.52) as a white solid. $^1$H NMR (400 MHz, DMSO-d$_6$) δ (ppm): 13.87 (s, 1H), 11.08 (s, 1H), 8.40 (s, 1H), 7.83 (d, 1H, J=8.0 Hz), 7.73 (d, 1H, J=8.0 Hz), 7.63 (d 1H), 6.93 (s, 1H), 6.85 (s, 1H), 5.20-5.23 (m, 1H), 2.09 (s, 3H), 1.48 (d, 3H, J=6.7 Hz), 1.40 (brs, 2H), 1.24 (brs, 2H); ESIMS m/z (M+1): 429.0; HPLC purity: 98.71%, SFC purity 99.20% and N-(1-(5-cyano-1H-pyrazol-3-yl)ethyl)-3-methyl-4-(1-(6-(trifluoromethyl)pyridin-3-yl)cyclopropyl)-1H-pyrrole-2-carboxamide, enantiomer II (Compound 18; 17 mg; retention time: 3.51) as white solid. $^1$H NMR (400 MHz, DMSO-d$_6$) δ (ppm): 13.87 (s, 1H), 11.09 (s, 1H), 8.40 (s, 1H), 7.84 (d, 1H, J=8.0 Hz), 7.73 (d, 1H, J=8.0 Hz), 7.63 (d 1H), 6.93 (s, 1H), 6.84 (s, 1H), 5.20-5.23 (m, 1H), 2.09 (s, 3H), 1.47 (d, 3H, J=6.7 Hz), 1.40 (brs, 2H), 1.24 (brs, 2H); ESIMS m/z (M+1): 428.9; HPLC purity: 99.57%, SFC purity 99.29%.

Preparation of N-(1-(1H-imidazol-4-yl)ethyl)-3-methyl-4-(1-(6-(trifluoromethyl)pyridin-3-yl)cyclopropyl)-1H-pyrrole-2-carboxamide (Compound 19)

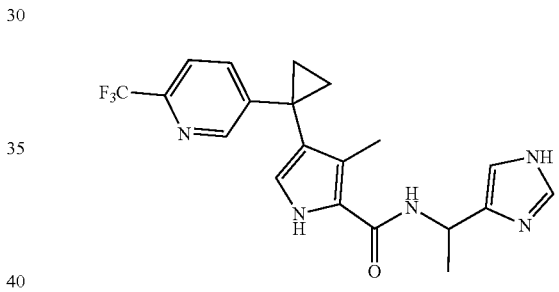

Compound 19 was synthesised by an analogous method to Scheme 3.

1-(1-((4-methylbenzyl)sulfonyl)-1H-imidazol-4-yl)ethan-1-amine (0.15 g, 0.58 mmol) and triethylamine (0.2 mL, 0.96 mmol) were added to a stirred solution of (9a) (0.15 g, 0.48 mmol) in dichloromethane (6 mL) at RT and continued stirring for 5 min. Then, HATU (0.27 g, 0.72 mmol) was added to the reaction mixture and stirred at same temperature for 16 h. After completion of reaction (monitored by TLC), water was added to reaction mixture and extracted with dichloromethane (2×10 mL). The combined organic layer was dried over Na$_2$SO$_4$ and concentrated. The resulting concentrated product was purified by column chromatography using 10-50% ethyl acetate in petroleum ether to afford 3-methyl-N-(1-(1-((4-methylbenzyl)sulfonyl)-1H-imidazol-4-yl)ethyl)-4-(1-(6-(trifluoromethyl)pyridin-3-yl)cyclopropyl)-1H-pyrrole-2-carboxamide (130 mg, 48%) as an off white solid.

TBAF (1.0 M THF) (0.6 mL, 0.56 mmol) was added to a stirred solution of 3-methyl-N-(1-(1-((4-methylbenzyl)sulfonyl)-1H-imidazol-4-yl)ethyl)-4-(1-(6-(trifluoromethyl)pyridin-3-yl)cyclopropyl)-1H-pyrrole-2-carboxamide (130 mg, 0.23 mmol) in THF (5 mL) at RT and stirred for 2 h at 50° C. After completion of reaction, reaction mixture was quenched saturated NaHCO$_3$ (5 mL) and extracted with dichloromethane (3×10 mL). The combined organic layers were dried (Na₂SO₄), filtered and concentrated. The resulting concentrated product was purified by column chromatography using 0-5% methanol in dichloromethane to afford N-(1-(1H-imidazol-4-yl)ethyl)-3-methyl-4-(1-(6-(trifluoromethyl)pyridin-3-yl)cyclopropyl)-1H-pyrrole-2-carboxamide (Compound 19; 70 mg, 74%) as an off white solid. $^1$H NMR (400 MHz, CD₃OD) δ (ppm): 8.35 (s, 1H), 7.67 (brs, 3H), 7.03 (s, 1H), 6.90 (s, 1H), 5.27 (q, 1H, J=6.6 Hz), 2.19 (s, 3H), 1.58 (d, 3H, J=6.6 Hz), 1.42-1.43 (m, 2H), 1.37-1.38 (m, 2H); ESIMS m/z (M+1): 404.1; LCMS: 99.04%; HPLC purity: 99.15%.

Compounds 20 and 21 (Enantiomers)

Racemic Compound 19 was separated by SFC to afford N-(1-(1H-imidazol-4-yl) ethyl)-3-methyl-4-(1-(6-(trifluoromethyl)pyridin-3-yl)cyclopropyl)-1H-pyrrole-2-carboxamide, enantiomer I (Compound 20; 20 mg; retention time: 2.34) as white solid. $^1$H NMR (400 MHz, CD₃OD) δ (ppm): 8.35 (s, 1H), 7.67 (brs, 3H), 7.03 (s, 1H), 6.90 (s, 1H), 5.27 (q, 1H, J=6.6 Hz), 2.19 (s, 3H), 1.58 (d, 3H, J=6.6 Hz), 1.42-1.43 (m, 2H), 1.37-1.38 (m, 2H); ESIMS m/z (M+1): 404.2; HPLC purity: 99.37%; SFC purity 100% and N-(1-(1H-imidazol-4-yl)ethyl)-3-methyl-4-(1-(6-(trifluoromethyl)pyridin-3-yl)cyclopropyl)-1H-pyrrole-2-carboxamide, enantiomer II (Compound 21; 25 mg; retention time: 3.94) as white solid. $^1$H NMR (400 MHz, CD₃OD) δ (ppm): 8.35 (s, 1H), 7.67 (brs, 3H), 7.03 (s, 1H), 6.90 (s, 1H), 5.26 (q, 1H, J=6.6 Hz), 2.19 (s, 3H), 1.58 (d, 3H, J=6.6 Hz), 1.43 (m, 2H), 1.37 (m, 2H); ESIMS m/z (M+1): 404.1; HPLC purity: 99.24%; SFC purity 100%.

Preparation of 4-(1-(6-(difluoromethyl)pyridin-3-yl) cyclopropyl)-3-methyl-N-(1-(1H-1,2,4-triazol-3-yl) ethyl)-1H-pyrrole-2-carboxamide (Compound 22)

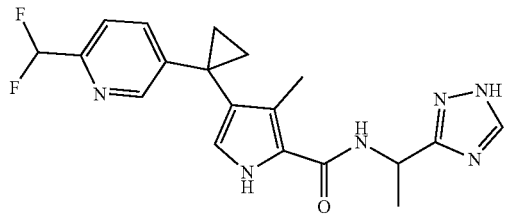 [SMILES: Cc1c(C2(c3ccc(C(F)F)nc3)CC2)c[nH]c1C(=O)NC(C)c1nc[nH]n1]

Compound 22 was synthesised by an analogous method to Scheme 3.

Step (i)

Pd(OAc)₂ (0.16 g, 0.72 mmol) and 4,5-bis(diphenylphosphino)-9, 9-dimethylxanthene (0.70 g, 1.2 mmol) were added to a purged solution of 5-bromo-2-(difluoromethyl) pyridine (5 g, 24.03 mmol), K₃PO₄ (15.3 g, 72.07 mmol) and N, O-dimethyl hydroxylamine hydrochloride (3.52 g, 36.09 mmol) in m-Xylene (70 mL) RT. It was heated to 100° C. for 16 h under CO gas. The reaction mixture was cooled to Rt, added 10% NaHCO₃ was added and extracted with ethyl acetate (3×100 mL). The concentrated product was purified by flash chromatography (silica gel, eluting with hexane:EtOAc mixtures from 100% to 60:40%) to afford 6-(difluoromethyl)-N-methoxy-N-methylpyridine-3-carboxamide (2c) (2.5 g, 48%) as white solid. $^1$H NMR (400 MHz, DMSO-d₆) δ (ppm): 8.91 (s, 1H), 8.26 (dd, 1H, J=2.0 Hz & 8.0 Hz), 7.81 (d, 1H, J=8.0 Hz), 6.79 (t, 1H, J=55.2 Hz), 3.62 (s, 3H), 3.33 (s, 3H); ESIMS m/z (M+1): 217.1.

Step (ii)

1-Propynylmagnesium bromide (0.5 M in THF) (28 mL, 13.89 mmol) was added to 6-(difluoromethyl)-N-methoxy-N-methylpyridine-3-carboxamide (2.5 g, 11.5 mmol) in THE (20 mL) at 0° C. and stirred for 2 h at RT. Reaction mixture was quenched with 1.5 N HCl solution and extracted with ethyl acetate (2×100 mL). The resulting organic layer was washed with brine, dried over Na₂SO₄ and concentrated to afford 1-(6-(difluoromethyl)pyridin-3-yl) but-2-yn-1-one (3c) (2.1 g, 93%) as yellow liquid. $^1$H NMR (400 MHz, DMSO-d₆) δ (ppm): 9.31 (s, 1H), 8.62 (dd, 1H, J=2.0 Hz & 8.4 Hz), 7.88 (d, 1H, J=8.4 Hz), 6.83 (t, 1H, J=55.2), 2.25 (s, 3H); ESIMS m/z (M+1): 196.0.

Step (iii)

Intermediate (3c) (2.0 g, 10.25 mmol) was added to stirred solution of silver carbonate (0.28 g, 1.02 mmol) in NMP (20 mL) at RT. Ethyl isocyanoacetate (1.8 g, 15.36 mmol) was added at room temperature and stirred for 2 h at 80° C. Reaction mixture was cooled to RT, quenched with water (100 mL), and extracted with ethyl acetate (2×100 mL). The combined organic layers were dried (Na₂SO₄), filtered and concentrated. The concentrated product was purified by flash chromatography (silica gel, eluting with hexane:EtOAc mixtures from 100% to 60:40%) to afford the title compound ethyl 4-(6-(difluoromethyl)pyridine-3-carbonyl)-3-methyl-1H-pyrrole-2-carboxylate (4c) (1.5 g, 47%) as an off white solid. $^1$H NMR (400 MHz, DMSO-d₆) δ (ppm): 8.93 (d, 1H, J=1.2 Hz), 8.30 (dd, 1H, J=1.2 Hz & 8.4 Hz), 7.85 (d, 1H, J=8.4 Hz), 7.34 (s, 1H), 6.69-6.97 (m, 1H), 4.34 (2H, q, J=7.2 Hz), 2.66 (s, 3H), 1. 45 (t, 3H, J=7.2 Hz). ESIMS m/z(M+1): 309.2.

Step (iv)

DMAP (56 mg, 0.49 mmol) was added to a stirred solution of intermediate (4c) (1.5 g, 4.87 mmol), Et3N (1.3 mL, 9.74 mmol) in CH₂Cl₂ (20 mL) at 0° C. for 10 min. Tosyl chloride (1.1 g, 5.84 mmol) was added at 0° C. and RT and stirred for 2 h at room temperature. 1.5 N HCl (100 mL) was added to reaction mixture and extracted with ethyl acetate (2×100 mL). The resulting combined organic layer was washed with brine, dried over Na₂SO₄ and concentrated. The concentrated product was purified by flash chromatography (silica gel, eluting with hexane:EtOAc mixtures from 100% to 80:20%) to afford ethyl 4-(6-(difluoromethyl) pyridine-3-carbonyl)-3-methyl-1-(4-methylbenzene-1-sulfonyl)-1H-pyrrole-2-carboxylate (5c) (2.0 g, 89%). $^1$H NMR (400 MHz, CD₃OD) δ(ppm): 9.03 (s, 1H), 8.39 (dd, 1H, J=1.6 Hz & 8.0 Hz), 8.03 (s, 1H), 7.89-7.94 (m, 3H), 7.46 (d, 2H, J=8.4 Hz), 6.72-6.99 (t, 1H, J=55.2 Hz), 4.31 (q, 2H, J=7.2 Hz), 2,47 (s, 6H), 1.31 (t, 3H, J=7.2 Hz); ESIMS m/z (M+1): 462.9.

Step (v)

Methyl magnesium bromide (1.0 M in THF) (6.5 mL, 6.49 mmol) was added to intermediate (5c) (2.0 g, 4.32 mmol) in THE (20 mL) at 0° C. and stirred for 2 h at RT. Reaction mixture was quenched with 1.5 N HCl solution and extracted with ethyl acetate (2×50 mL). The resulting organic layer was washed with brine, dried over Na₂SO₄ and concentrated to afford ethyl 4-(1-(6-(difluoromethyl)pyridin-3-yl)-1-hydroxyethyl)-3-methyl-1-(4-methylbenzene-1-sulfonyl)-1H-pyrrole-2-carboxylate (6c) (1.7 g, 85%) as colorless liquid. ESIMS m/z (M+1): 479.1. Product was taken into the next step without purification.

Step (vi)

Iodine (150 mg, catalytic amount) was added to intermediate (6c) (1.7 g, 3.55 mmol) in toluene (20 mL) at RT and stirred for 16 h at 115° C. Reaction mixture was quenched with 10% Na₂S₂O₃ solution and extracted with ethyl acetate (2×50 mL). The resulting organic layer was washed with brine, dried over Na$_2$SO$_4$ and concentrated. The concentrated product was purified by flash chromatography (silica gel, eluting with hexane:EtOAc from 100% to 90:10%) to afford ethyl 4-(1-(6-(difluoromethyl)pyridin-3-yl)ethenyl)-3-methyl-1-(4-methylbenzene-1-sulfonyl)-1H-pyrrole-2-carboxylate (7c) (1.0 g, 61%) as grey solid. $^1$H NMR (400 MHz, DMSO-d$_6$) δ (ppm): 8.60 (d, 1H, J=1.6 Hz), 7.87-7.92 (m, 3H), 7.71 (d, 1H, J=8.0 Hz), 7.65 (s, 1H), 7.46 (d, 2H, J=8.0 Hz), 6.76 (t, 1H, J=55.2 Hz), 5.88 (s, 1H), 5.58 (s, 1H), 4.26 (q, 2H, J=7.2 Hz), 2.48 (s, 3H), 1.93 (s, 3H), 1.26 (t, 3H, J=7.2 Hz); ESIMS m/z (M−1): 459.2.

Step (vii) To stirred solution of intermediate (7c) (1.0 g, 2.17 mmol) in THF (10 mL) was added to a stirred solution of trimethylsulfoxonium iodide (0.96 g, 4.34 mmol) and $^t$BuOK (0.49 g, 4.34 mmol) in DMSO (4 mL) at 0° C. and stirred for 4 h at RT. Reaction mixture was poured in to water (20 mL) and extracted with ethyl acetate (2×50 mL). The combined organic layers were dried (Na$_2$SO$_4$), filtered and concentrated. The concentrated product was purified by flash chromatography (silica gel, eluting with hexane:EtOAc mixtures from 100% to 60:40%) to afford ethyl 4-(1-(6-(difluoromethyl)pyridin-3-yl)cyclopropyl)-3-methyl-1-(4-methylbenzene-1-sulfonyl)-1H-pyrrole-2-carboxylate (8c) (0.6 g, 60%) as off white solid. $^1$H NMR (400 MHz, DMSO-d$_6$) δ (ppm): 8.28 (d, 1H, J=7.2 Hz), 7.85 (d, 2H, J=8.4 Hz), 7.69 (s, 1H), 7.58-7.65 (m, 2H), 7.44 (d, 2H, J=8.4 Hz), 6.69 (t, 1H, J=55.2 Hz), 4.23 (q, 2H, J=7.2 Hz), 2.47 (s, 3H), 1.44-1.45 (m, 2H), 1.38-1.40 (m, 2H), 1.25 (t, 3H, J=7.2 Hz); ESIMS m/z (M+1): 475.2.

Step (viii)

Sodium hydroxide (0.20 g, 5.02 mmol) was added to a stirred solution of intermediate (8c) (0.6 g, 1.25 mmol) in EtOH:water (8:2 mL) at RT and heated to 80° C. for 2 h. The resulting reaction mixture was concentrated and quenched with water (10 mL). Then, it was acidified with 10% citric acid solution. The solid obtained was filtered, washed with water and dried to afford 4-(1-(6-(difluoromethyl)pyridin-3-yl)cyclopropyl)-3-methyl-1H-pyrrole-2-carboxylic acid (9c) (0.25 g, 68%) as an off white solid. ESIMS (M+1) m/z: 293.2. the product was used directly without further purification.

Step (ix)

1-(1-Triphenylmethyl-1H-1, 2, 4-triazol-3-yl)ethan-1-amine (0.2 g, 0.58 mmol) and triethylamine (0.14 mL, 0.94 mmol) were added to a stirred solution of intermediate (9c) (0.14 g, 0.48 mmol) in dichloromethane (6 mL) at RT and continued stirring for 5 min. Then, HATU (0.27 g, 0.71 mmol) was added to the reaction mixture and stirred at same temperature for 5 h. After completion of reaction (monitored by TLC), water was added to reaction mixture and extracted with dichloromethane (2×20 mL). The combined organic layer was dried over Na$_2$SO$_4$ and concentrated. The resulting concentrated product was purified by column chromatography using 10-50% ethyl acetate in petroleum ether to afford 4-(1-(6-(difluoromethyl)pyridin-3-yl)cyclopropyl)-3-methyl-N-(1-(1-(triphenylmethyl)-1H-1,2,4-triazol-3-yl)ethyl)-1H-pyrrole-2-carboxamide (140 mg, 45%) as gummy solid.

To the intermediate solid (140 mg, 0.22 mmol) in TFA (0.8 mL, 4 vol) and CH$_2$Cl$_2$ (1 mL) was added triethylsilane (0.38 mL, 2 vol) at RT and continued for 1 h. After completion of reaction, reaction mixture was quenched sat. NaHCO$_3$ (5 mL) by dropwise addition at 0° C. and extracted with dichloromethane (3×10 mL). The combined organic layers were dried (Na$_2$SO$_4$), filtered and concentrated. The resulting concentrated product was purified by column chromatography using 0-5% methanol in dichloromethane to afford 4-(1-(6-(difluoromethyl)pyridin-3-yl)cyclopropyl)-3-methyl-N-(1-(1H-1,2,4-triazol-3-yl)ethyl)-1H-pyrrole-2-carboxamide (Compound 22; 70 mg, 81%) as an off white solid. $^1$H NMR (400 MHz, DMSO-d6) δ (ppm): 13.81 (s, 1H), 11.13 (s, 1H), 8.50-8.60 (m, 1H), 8.32 (d, 1H, J=2.0 Hz), 7.80-7.90 (m, 1H), 7.53-7.60 (m, 2H), 6.75-7.05 (m, 2H), 5.22-5.26 (m, 1H), 2.11 (s, 3H), 1.49 (d, 3H, J=6.8 Hz), 1.23-1.35 (m, 4H); ESIMS m/z (M+1): 387.1; LCMS: 97.97%; HPLC purity: 97.71%.

Compounds 23 and 24 (Enantiomers)

Racemic Compound 22 was separated by SFC to afford 4-(1-(6-(difluoromethyl)pyridin-3-yl)cyclopropyl)-3-methyl-N-(1-(1H-1,2,4-triazol-3-yl)ethyl)-1H-pyrrole-2-carboxamide, enantiomer I (Compound 23; 13 mg; retention time: 1.29) as an off white solid. $^1$H NMR (400 MHz, CD$_3$OD) δ (ppm): 8.30 (d, 1H, J=2.0 Hz), 7.66 (dd, 1H, J=2.0 Hz & 8.4 Hz), 7.56 (d, 1H, J=8.0 Hz), 6.93 (s, 1H), 6.68 (t, 1H, J=55.2 Hz), 5.38 (q, 1H, J=6.8 Hz), 2.21 (s, 3H), 1.64 (d, 3H, J=6.8 Hz), 1.39-1.41 (m, 2H), 1.32-1.34 (m, 2H); ESIMS m/z (M+1): 387.2; HPLC purity: 99.50%; SFC purity 100% and 4-(1-(6-(difluoromethyl)pyridin-3-yl)cyclopropyl)-3-methyl-N-(1-(1H-1,2,4-triazol-3-yl)ethyl)-1H-pyrrole-2-carboxamide enantiomer II (Compound 24; 35 mg; retention time: 1.99) as an off white solid. $^1$H NMR (400 MHz, CD$_3$OD) δ (ppm): 8.30 (d, 1H, J=2.0 Hz), 7.66 (dd, 1H, J=2.0 Hz & 8.4 Hz), 7.56 (d, 1H, J=8.0 Hz), 6.93 (s, 1H), 6.68 (t, 1H, J=55.2 Hz), 5.38 (q, 1H, J=6.8 Hz), 2.21 (s, 3H), 1.64 (d, 3H, J=6.8 Hz), 1.39-1.41 (m, 2H), 1.32-1.34 (m, 2H); ESIMS m/z (M+1): 387.2; HPLC purity: 96.03%; SFC purity 99.16.

Preparation of 4-{1-[3-cyano-4-(trifluoromethyl)phenyl]cyclopropyl}-3-methyl-N-[1-(1H-1,2,4-triazol-3-yl)ethyl]-1H-pyrrole-2-carboxamide (Compound 25)

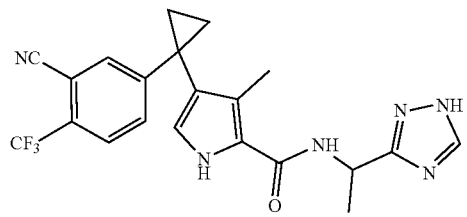 [SMILES: Cc1c(C2(c3ccc(C(F)(F)F)c(C#N)c3)CC2)c[nH]c1C(=O)NC(C)c1nc[nH]n1]

Compound 25 was synthesised by an analogous method to Scheme 3.

Potassium cyanide (1.16 g, 17.81 mmol) was added to a stirred solution of racemic compound 4 (3.0 g, 7.13 mmol) in DMSO (20 mL) at RT. Then, the reaction mixture was stirred for 20 h at 130° C. Starting material was not consumed. The continuation of reaction lead to side product formation. Therefore, the reaction mixture was quenched with water (200 mL) and extracted with ethyl acetate (3×200 mL). The combined organic layers were dried (Na$_2$SO$_4$), filtered and concentrated. The resulting concentrated product was purified by preparative HPLC to afford 4-{1-[3-cyano-4-(trifluoromethyl)phenyl]cyclopropyl}-3-methyl-N-[1-(1H-1,2,4-triazol-3-yl)ethyl]-1H-pyrrole-2-carboxamide (Compound 25, 550 mg, 18%) as white solid. $^1$H NMR (400 MHz, CD$_3$OD) δ (ppm): 8.34 (brs, 1H), 7.71 (d, 1H, J=8.4 Hz), 7.54 (s, 1H), 7.47 (d, 1H, J=8.4 Hz), 6.89 (s, 1H), 5.35-5.37 (m, 1H), 2.19 (s, 3H), 1.61 (d, 3H, J=6.8 Hz), 1.41-1.42 (m, 2H), 1.34-1.36 (m, 2H); ESIMS m/z (M+1): 429.2; LCMS: 97.67%; HPLC purity: 97.55%.

Compounds 26 and 27 (Enantiomers)

Compound 25 was separated by SFC purification to afford 4-{1-[3-cyano-4-(trifluoromethyl)phenyl]cyclopropyl}-3-methyl-N-[1-(1H-1,2,4-triazol-3-yl)et hyl]-1H-pyrrole-2-carboxamide, enantiomer I (Compound 26; 222 mg; retention time: 1.70) as an off white solid. ¹H NMR (400 MHz, CD₃OD) δ(ppm): 8.28 (brs, 1H), 7.75 (d, 1H, J=8.4 Hz), 7.57 (s, 1H), 7.49-7.51 (d, 1H, J=8.4 Hz), 6.92 (s, 1H), 5.36-5.41 (m, 1H), 2.18 (s, 3H), 1.64 (d, 3H, J=6.8 Hz), 1.43-1.45 (m, 2H), 1.37-1.40 (m, 2H); ESIMS (m/z) (M+1): 429.1; HPLC purity: 99.92; SFC purity 100%, and 4-{1-[3-cyano-4-(trifluoromethyl) phenyl]cyclopropyl}-3-methyl-N-[1-(1H-1,2,4-triazol-3-yl)ethyl]-1H-pyrrole-2-carboxamide; enantiomer II (Compound 27; 190 mg; retention time: 3.15)) as an off white solid. ¹H NMR (400 MHz, CD₃OD) δ(ppm): 8.28 (brs, 1H), 7.75 (d, 1H, J=8.4 Hz), 7.57 (s, 1H), 7.49-7.51 (d, 1H, J=8.4 Hz), 6.92 (s, 1H), 5.38 (m, 1H), 2.19 (s, 3H), 1.64 (d, 3H, J=6.8 Hz), 1.43-1.46 (m, 2H), 1.37-1.40 (m, 2H); ESIMS (m/z): 429.1; HPLC purity: 99.38%; SFC purity 100%.

The title compounds are also synthesized as described in the general synthetic route, Scheme 4 below:

Scheme 4

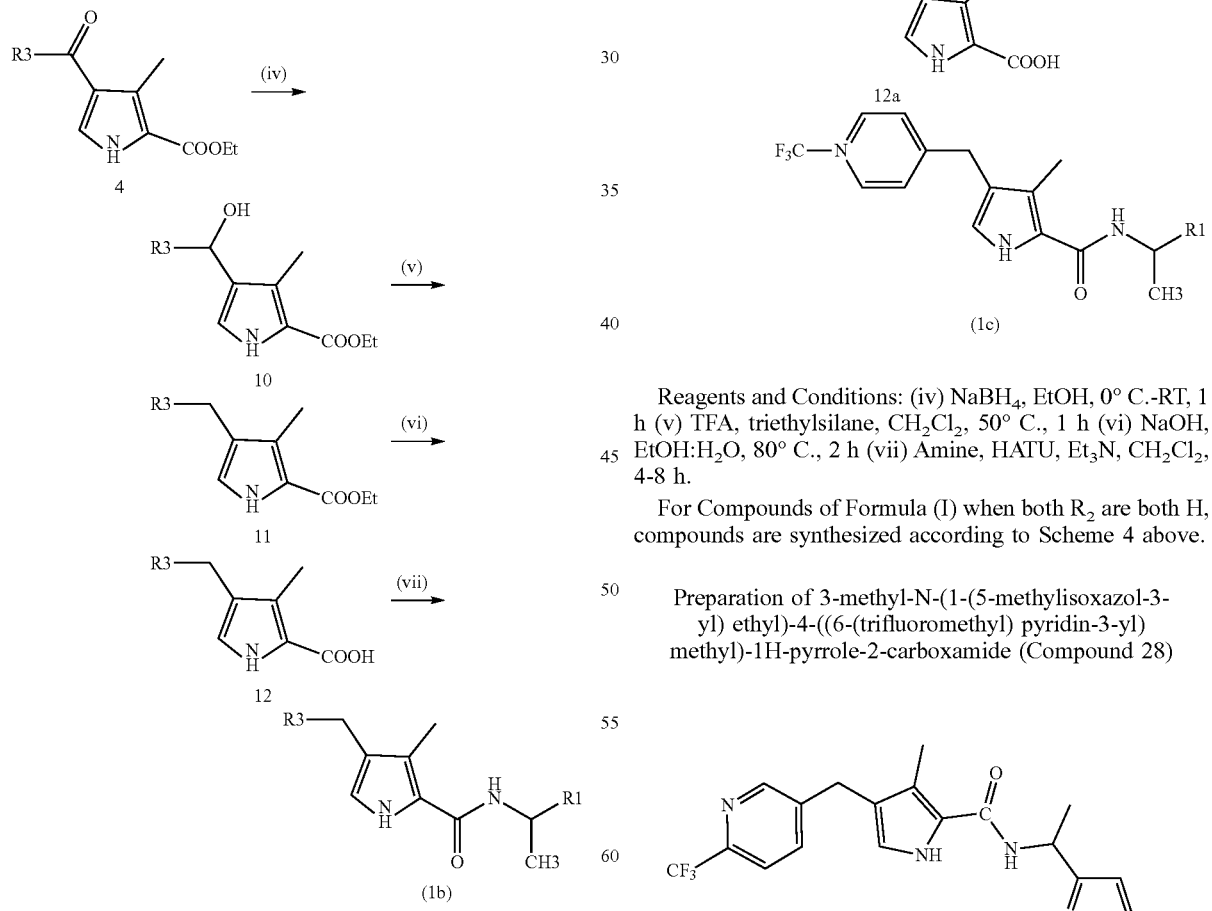

Reagents and Conditions: (iv) NaBH₄, EtOH, 0° C.-RT, 1 h (v) TFA, triethylsilane, CH₂Cl₂, 50° C., 1 h (vi) NaOH, EtOH:H₂O, 80° C., 2 h (vii) Amine, HATU, Et₃N, CH₂Cl₂, 4-8 h.

Scheme 5

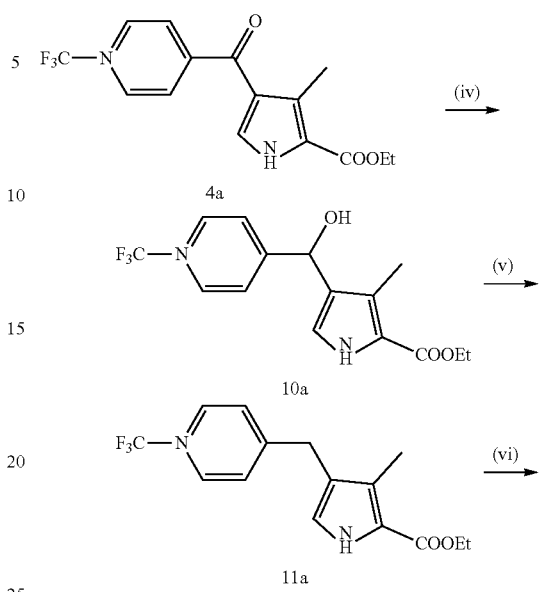

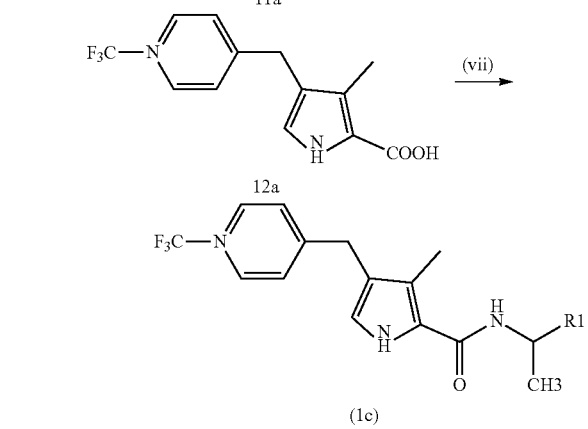

Reagents and Conditions: (iv) NaBH₄, EtOH, 0° C.-RT, 1 h (v) TFA, triethylsilane, CH₂Cl₂, 50° C., 1 h (vi) NaOH, EtOH:H₂O, 80° C., 2 h (vii) Amine, HATU, Et₃N, CH₂Cl₂, 4-8 h.

For Compounds of Formula (I) when both R₂ are both H, compounds are synthesized according to Scheme 4 above.

Preparation of 3-methyl-N-(1-(5-methylisoxazol-3-yl) ethyl)-4-((6-(trifluoromethyl) pyridin-3-yl) methyl)-1H-pyrrole-2-carboxamide (Compound 28)

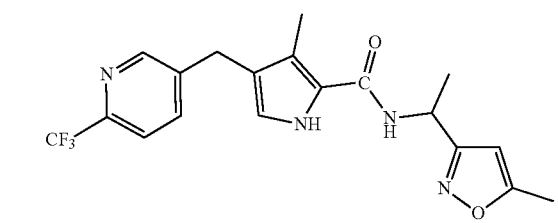 [SMILES: Cc1cc(C(C)NC(=O)c2[nH]cc(Cc3ccc(C(F)(F)F)nc3)c2C)no1]

Compound 28 was synthesised by an analogous method to Scheme 4, in particular Scheme 5.

Step (iv)

Sodium borohydride (1.43 g, 36.78 mmol) was added portionwise to a stirred solution of intermediate (4a) (6 g, 18.39 mmol) in ethanol (50 mL) at 0° C. Then, the reaction mixture was stirred for 1 h at room temperature and was concentrated under reduced pressure. Water (20 mL) was added to reaction mixture and extracted with ethyl acetate (2×200 mL). The resulting combined organic layer was washed with brine, dried over $Na_2SO_4$ and concentrated to afford ethyl 4-(hydroxy(6-(trifluoromethyl) pyridin-3-yl) methyl)-3-methyl-1H-pyrrole-2-carboxylate (10a) (5.6 g, 93%). It was taken for the next step without any purification.

Step (v)

To a stirred solution of intermediate (10a) (5.5 g, 16.75 mmol) in TFA (8 mL, 100.5 mmol) was added triethylsilane (5.8 g, 50.25 mmol) at RT and stirred at 85° C. for 1 h. Then, saturated $NaHCO_3$ (50 mL) was added dropwise at 0° C. and extracted with ethyl acetate (3×100 mL, with careful venting). The combined organic layers were dried ($Na_2SO_4$), filtered and concentrated. The resulting concentrated product was triturated with petroleum ether to afford ethyl 3-methyl-4-((6-(trifluoromethyl) pyridin-3-yl)methyl)-1H-pyrrole-2-carboxylate (11a) (4 g, 77%) as white solid. $^1$H NMR (300 MHz, DMSO-$d_6$) δ(ppm): 11.41 (s, 1H), 8.64 (s, 1H), 7.81 (brs, 2H), 6.81 (s, 1H), 4.21 (q, 2H, J=7.1 Hz), 3.87 (s, 2H), 2.15 (s, 3H), 1.27 (t, 3H, J=7.1 Hz); ESIMS m/z: 314.2.

Step (vi)

Sodium hydroxide (1 g, 25.61 mmol) was added to a stirred solution of intermediate (11a) (4.0 g, 12.80 mmol) in EtOH:$H_2O$ (32:8 mL) at RT and heated to 80° C. for 2 h. The resulting reaction mixture was concentrated and quenched with water (10 mL). Then, it was acidified with 10% citric acid solution. The solid obtained was filtered, washed with water and dried to afford 3-methyl-4-((6-(trifluoromethyl) pyridin-3-yl)methyl)-1H-pyrrole-2-carboxylic acid (12a) (3.2 g, 88%) as an off white solid. $^1$H NMR (300 MHz, DMSO-$d_6$) δ (ppm): 12.15 (s, 1H), 11.29 (s, 1H), 8.64 (s, 1H), 7.81 (brs, 2H), 6.75 (s, 1H), 3.86 (s, 2H), 2.14 (s, 3H); ESIMS m/z (M+1): 285.2.

Step (vii)

1-(5-Methylisoxazol-3-yl)ethan-1-amine (97 mg, 0.84 mmol) (PCT Int Appl. 2010, WO 2010/131145 A1) and triethylamine (0.2 mL, 1.40 mmol) were added to a stirred solution of intermediate (12a) (200 mg, 0.70 mmol) in dichloromethane (4 mL) at RT and continued for 5 min. Then, HATU (400 mg, 1.05 mmol) was added to the reaction mixture and stirred at same temperature for 4 h. After completion of reaction (monitored by TLC), water was added to reaction mixture and extracted with dichloromethane (2×60 mL). The combined organic layer was dried over $Na_2SO_4$ and concentrated. The resulting concentrated product was purified by column chromatography using 10-50% ethyl acetate in petroleum ether to afford 3-methyl-N-(1-(5-methylisoxazol-3-yl) ethyl)-4-((6-(trifluoromethyl)pyridin-3-yl)methyl)-1H-pyrrole-2-carboxamide (Compound 28; 160 mg, 55%) as an off white solid. $^1$H NMR (400 MHz, DMSO-$d_6$) δ (ppm): 11.02 (s, 1H), 8.63 (s, 1H), 7.81 (s, 2H), 7.80 (d, 1H), 6.73 (s, 1H), 6.18 (s, 1H), 5.13-5.17 (m, 1H), 3.86 (s, 2H), 2.34 (s, 3H), 2.14 (s, 3H), 1.44 (d, 3H); ESIMS m/z: 393.2; LCMS: 97.21%; HPLC purity: 98.59%.

Compounds 29 and 30 (Enantiomers)

Racemic Compound 28 was separated by SFC to afford 3-methyl-N-(1-(5-methylisoxazol-3-yl)ethyl)-4-((6-(trifluoromethyl)pyridin-3-yl)methyl)-1H-pyrrole-2-carboxamide, enantiomer I (Compound 29; 104 mg, retention time 3.13) as an off white solid; $^1$H NMR (400 MHz, DMSO-$d_6$) δ(ppm): 11.02 (s, 1H), 8.63 (s, 1H), 7.81 (s, 2H), 7.80 (d, 1H), 6.73 (s, 1H), 6.18 (s, 1H), 5.13-5.17 (m, 1H), 3.86 (s, 2H), 2.34 (s, 3H), 2.14 (s, 3H), 1.44 (d, 3H); ESIMS m/z: 393.2; HPLC purity: 98.57%; SFC purity 100% and 3-methyl-N-(1-(5-methylisoxazol-3-yl)ethyl)-4-((6-(trifluoromethyl)pyridin-3-yl)methyl)-1H-pyrrole-2-carboxamide, enantiomer II (Compound 30; 70 mg, retention time 4.0) as an off white solid. $^1$H NMR (400 MHz, DMSO-$d_6$) δ(ppm): 11.02 (s, 1H), 8.63 (s, 1H), 7.81 (s, 2H), 7.80 (d, 1H), 6.73 (s, 1H), 6.18 (s, 1H), 5.13-5.17 (m, 1H), 3.86 (s, 2H), 2.34 (s, 3H), 2.14 (s, 3H), 1.44 (d, 3H); ESIMS m/z (M+1): 393.2; HPLC purity: 98.96%; SFC purity 100%.

Preparation of 3-methyl-N-(1-(1H-pyrazol-4-yl)ethyl)-4-((6-(trifluoromethyl)pyridin-3-yl)methyl)-1H-pyrrole-2-carboxamide (Compound 31)

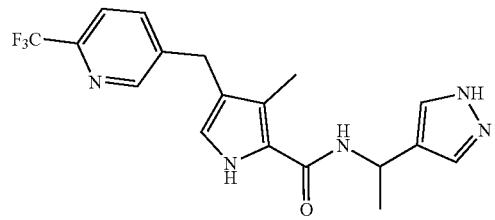 [SMILES: Cc1c(Cc2ccc(C(F)(F)F)nc2)c[nH]c1C(=O)NC(C)c1cn[nH]c1]

Compound 31 was synthesised by an analogous method to Scheme 4.

1-(1-(triphenylmethyl)-1H-pyrazol-4-yl)ethan-1-amine (0.86 g, 2.53 mmol) and triethylamine (0.6 mL, 4.22 mmol) were added to a stirred solution of intermediate (12a) (600 mg, 2.11 mmol) in dichloromethane (20 mL) at RT and continued stirring for 5 min. Then, HATU (1.2 g, 3.16 mmol) was added to the reaction mixture and stirred at same temperature for 8 h. After completion of reaction (monitored by TLC), water was added to reaction mixture and extracted with dichloromethane (2×50 mL). The combined organic layer was dried over $Na_2SO_4$ and concentrated. The resulting concentrated product was purified by column chromatography using 10-50% ethyl acetate in petroleum ether to afford 3-methyl-4-((6-(trifluoromethyl)pyridin-3-yl) methyl)-N-(1-(1-triphenylmethyl-1H-pyrazol-4-yl)ethyl)-1H-pyrrole-2-carboxamide (300 mg, 23%) as gummy solid that was taken directly into the next step.

To a stirred solution of 3-methyl-4-((6-(trifluoromethyl) pyridin-3-yl) methyl)-N-(1-(1-triphenylmethyl-1H-pyrazol-4-yl)ethyl)-1H-pyrrole-2-carboxamide (0.3 g, 0.48 mmol) in TFA (1.20 mL, 4 vol) was added triethylsilane (0.6 mL, 2 vol) at RT and stirred for 1 h. The reaction mixture was quenched with saturated $NaHCO_3$ (50 mL) by dropwise addition at 0° C. and extracted with dichloromethane (3×100 mL). The combined organic layers were dried ($Na_2SO_4$), filtered and concentrated. The resulting concentrated product was purified by column chromatography using 0-5% methanol in dichloromethane to afford 3-methyl-N-(1-(1H-pyrazol-4-yl)ethyl)-4-((6-(trifluoromethyl)pyridin-3-yl) methyl)-1H-pyrrole-2-carboxamide (Compound 31; 0.15 g, 82%) as white solid. $^1$H NMR (400 MHz, $CD_3OD$) δ (ppm): 8.40 (s, 1H), 7.65 (d, 1H, J=8.2 Hz), 7.56 (d, 1H, J=8.2 Hz), 7.46 (brs, 2H), 6.54 (s, 1H), 5.09 (q, 1H, J=6.8 Hz), 3.79 (s, 2H), 2.04 (s, 3H), 1.41 (d, 3H, J=6.8 Hz); ESIMS m/z (M+1): 378; LCMS: 99.90%; HPLC purity: 96.45%.

Compounds 32 and 33 (Enantiomers)

Racemic Compound 31 was separated by SFC to afford 3-methyl-N-(1-(1H-pyrazol-4-yl)ethyl)-446-(trifluoromethyl)pyridin-3-yl)methyl)-1H-pyrrol e-2-carboxamide, enantiomer I (Compound 32; 76 mg, retention time 2.94) as an off white solid. $^1$H NMR (400 MHz, CD$_3$OD)67 (ppm): 8.56 (s, 1H), 7.81 (d, 1H, J=8.2 Hz), 7.71 (d, 1H, J=8.2 Hz), 7.61 (brs, 2H), 6.70 (s, 1H), 5.25 (q, 1H, J=6.8 Hz), 3.94 (s, 2H), 2.19 (s, 3H), 1.57 (d, 3H, J=6.8 Hz); ESIMS m/z (M+1): 378.2; HPLC purity: 98.61%; SFC purity 99.72% and 3-methyl-N-(1-(1H-pyrazol-4-yl)ethyl)-4-((6-(trifluoromethyl) pyridin-3-yl)methyl)-1H-pyrrole-2-carboxamide, enantiomer II (Compound 33; 74 mg, retention time 4.27) as an off white solid. $^1$H NMR (400 MHz, CD$_3$OD) δ(ppm): 8.56 (s, 1H), 7.81 (d, 1H, J=8.2 Hz), 7.71 (d, 1H, J=8.2 Hz), 7.61 (brs, 2H), 6.70 (s, 1H), 5.25 (q, 1H, J=6.8 Hz), 3.94 (s, 2H), 2.19 (s, 3H), 1.57 (d, 3H, J=6.8 Hz); ESIMS m/z (M+1): 378.2; HPLC purity: 98.52%; SFC purity 99.74%.

Preparation of 3-methyl-N-(1-(1-methyl-1H-pyrazol-4-yl)ethyl)-4-((6-(trifluoromethyl) pyridin-3-yl)methyl)-1H-pyrrole-2-carboxamide (Compound 34)

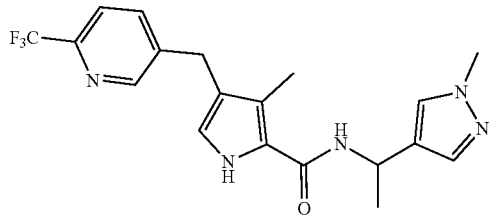 [SMILES: Cc1c(Cc2ccc(C(F)(F)F)nc2)c[nH]c1C(=O)NC(C)c1cnn(C)c1]

Compound 34 was synthesised by an analogous method to Scheme 4.

1-(1-methyl-1H-pyrazol-4-yl)ethan-1-amine (CAS 911788-33-5) (48 mg, 0.39 mmol) and triethylamine (0.1 mL, 0.70 mmol) were added to a stirred solution of intermediate (12a) (100 mg, 0.35 mmol) in dichloromethane (3 mL) at RT and continued stirring for 5 min. Then, HATU (200 mg, 0.53 mmol) was added to the reaction mixture and stirred at same temperature for 4 h. After completion of reaction (monitored by TLC), water was added to reaction mixture and extracted with dichloromethane (2×20 mL). The combined organic layer was dried over Na$_2$SO$_4$ and concentrated. The resulting concentrated product was purified by column chromatography using 10-50% ethyl acetate in petroleum ether to afford 3-methyl-N-(1-(1-methyl-1H-pyrazol-4-yl)ethyl)-4-((6-(trifluoromethyl)pyridin-3-yl) methyl)-1H-pyrrole-2-carboxamide (Compound 34; 80 mg, 58%) as an off white solid. $^1$H NMR (400 MHz, CDCl$_3$) δ (ppm): 9.19 (bs, 1H), 8.60 (s, 1H), 7.61 (m, 2H), 7.48 (s, 1H), 7.37 (s, 1H), 6.67 (s, 1H), 5.78-5.80 (m, 1H), 5.30-5.34 (m, 1H), 3.90 (m, 5H), 2.14 (s, 3H), 1.59 (d, 3H); ESIMS m z (M+1): 392; LCMS: 99.89%; HPLC purity: 97.61%.

Compounds 35 and 36 (Enantiomers)

Racemic Compound 34 was separated by SFC to afford 3-methyl-N-(1-(1-methyl-1H-pyrazol-4-yl)ethyl)-4-((6-(trifluoromethyl)pyridin-3-yl)methyl)-1 H-pyrrole-2-carboxamide, enantiomer I (Compound 35; 110 mg, retention time 3.13) as an off white solid. $^1$H NMR (400 MHz, CDCl$_3$) δ(ppm): 9.15 (bs, 1H), 8.60 (s, 1H), 7.61 (m, 2H), 7.51 (s, 1H), 7.29 (s, 1H), 6.67 (s, 1H), 5.81 (m, 1H), 5.32 (m, 1H), 3.92-3.90 (m, 5H), 2.14 (s, 3H), 1.59 (d, 3H); ESIMS m/z (M+1): 392.2; HPLC purity: 97.58%, SFC purity 99.19% and 3-methyl-N-(1-(1-methyl-1H-pyrazol-4-yl)ethyl)-4-((6-(trifluoromethyl)pyri din-3-yl)methyl)-1 H-pyrrole-2-carboxamide, enantiomer II (Compound 36; 105 mg, retention time 5.07) as an off white solid. $^1$H NMR (400 MHz, CDCl$_3$) δ(ppm): 9.23 (bs, 1H), 8.60 (s, 1H), 7.61 (m, 2H), 7.51 (s, 1H), 7.41 (s, 1H), 6.67 (s, 1H), 5.82 (m, 1H), 5.32 (m, 1H), 3.90 (m, 5H), 2.14 (s, 3H), 1.59 (d, 3H); ESIMS m/z (M+1): 392.2; HPLC purity: 99.00%, SFC purity 98.75%.

Intermediate Preparation 1-(1-(Triphenylmethyl)-1H-1, 2, 4-triazol-3-yl) ethan-1-amine Step (i) 1,1'-Carbonyldiimidazole (0.65 g, 4.05 mmol) was added to a stirred solution of 1-(triphenylmethyl)-1H-1,2,4-triazole-3-carboxylic acid (Hiroshi et al., 2017, *J. Med. Chem.*, 60 (2), 608-626) (1.2 g, 3.37 mmol) in DMF (20 mL) at RT for 1 h. Then N, O-dimethyl hydroxylamine hydrochloride (0.5 g, 5.06 mmol) was added at room temperature for 6 h. Completion of the reaction was confirmed by UPLC. The reaction mixture was poured into water and extracted with ethyl acetate (2×50 mL). The combined organic layers were dried (Na$_2$SO$_4$), filtered and concentrated. The concentrated product was purified by flash chromatography (silica gel, eluting with hexane:EtOAc mixtures from 100% to 60:40%) to afford N-methoxy-N-methyl-1-(triphenylmethyl)-1H-1, 2, 4-triazole-3-carboxamide (1.0 g, 75%). 1H NMR (400 MHz, DMSO d$_6$) δ (ppm): 8.33 (s, 1H), 7.41-7.45 (m, 9H), 7.08-7.10 (m, 6H), 3.55 (s, 3H), 3.25 (s, 3H).

Step (ii)

Methyl magnesium bromide solution (3.0 M in THF, 0.92 mL, 2.76 mmol) was added to a stirred solution of N-methoxy-N-methyl-1-(triphenylmethyl)-1H-1, 2, 4-triazole-3-carboxamide (1.0 g, 2.51 mmol) in THE (20 mL) at 0° C. and stirred for 2 h at room temperature. Completion of the reaction was confirmed by UPLC. Reaction mixture was quenched with 1.5 N HCl solution and extracted with ethyl acetate (2×30 mL). The resulting organic layer was washed with brine solution, dried over Na$_2$SO$_4$ and concentrated to afford 1-(1-(triphenylmethyl)-1H-1, 2, 4-triazol-3-yl)ethan-1-one (0.7 g, 80%) as a colorless liquid. 1H NMR (400 MHz, CDCl$_3$) δ (ppm): 8.06 (s, 1H), 7.31-7.37 (m, 9H), 7.14-7.17 (m, 6H), 2.45 (s, 3H).

Step (iii)

Titanium (IV) isopropoxide (1.1 g, 2.93 mmol) was added to a stirred solution of 1-(1-(triphenylmethyl)-1H-1, 2, 4-triazol-3-yl)ethan-1-one (0.7 g, 1.97 mmol) in 7N methanolic ammonia (5 mL) at 0° C. and stirred at room temperature for 4 h. Then, sodium borohydride (0.15 g, 3.94 mmol) was added at 0° C. and stirred at room temperature and continued stirring for 4 h. Completion of the reaction was confirmed by UPLC. Then reaction mixture was concentrated. Saturated sodium bicarbonate solution (10 mL) was added to the concentrated product and the aqueous mixture extracted with ethyl acetate (2×50 mL). The resulting extract combined organic layer was washed with brine, dried over Na$_2$SO$_4$ and concentrated to afford 1-(1-(triphenylmethyl)-1H-1,2,4-triazol-3-yl)ethan-1-amine (0.4 g, 57%) as a gummy liquid. 1H NMR (400 MHz, DMSO-d$_6$) δ (ppm): 7.94 (s, 1H), 7.36-7.40 (m, 9H), 7.04-7.07 (m, 6H), 4.00 (q, 1H, J=6.8 Hz), 1.30 (d, 3H, J=6.8 Hz).

1-(1-(Triphenylmethyl)-1H-pyrazol-4-yl)ethan-1-amine

Titanium (IV) isopropoxide (1.6 g, 5.66 mmol) was added to a stirred solution of 1-(1-(1-(triphenylmethyl)-1H-pyrazol-4-yl)ethan-1-one (WO 2006/014005) (1.0 g, 2.83 mmol) in 7N methanolic ammonia (10 mL) at 0° C. and stirred at room temperature for 4 h. Then, sodium borohydride (0.21 g, 5.66 mmol) was added at 0° C. and stirred at room temperature and continued stirring for 4 h. Completion of the reaction was confirmed by UPLC. Then organic solvent was concentrated under reduced pressure. Reaction mixture was quenched with saturated sodium bicarbonate solution (20 mL) and extracted with ethyl acetate (2×50 mL). The resulting extract combined organic layer was washed with brine, dried over $Na_2SO_4$ and concentrated to afford 1-(1-(triphenylmethyl)-1H-pyrazol-4-yl)ethan-1-amine (0.5 g, 48%) as yellow liquid. 1H NMR (400 MHz, DMSO-$d_6$) δ (ppm): 7.54 (s, 1H), 7.36-7.40 (m, 9H), 7.20 (s, 1H), 7.04-7.07 (m, 6H), 4.66-4.69 (m, 1H), 1.29 (d, 3H, J=6.8 Hz).

1-(1-(4-Methylbenzene-1-sulphonyl)-1H-imidazol-4-yl)ethan-1-amine $NaBH_3CN$ (171 mg, 2.72 mmol) was added to a stirred solution of 1-(1-(4-methylbenzene-1-sulfonyl)-1H-imidazol-4-yl)ethan-1-one (Sandtorv, 2015, *European Journal of Organic Chemistry*, (16), 3506-3512) (600 mg, 2.27 mmol) and NH4OAc (1.75 g, 22.72 mmol) in $CH_3OH$ (20 mL) at RT and heated for 4 h at 50° C. The reaction mixture was then concentrated and the reaction mixture was taken in $NaHCO_3$ solution (20 mL) extracted with ethyl acetate (2×50 mL). The combined organic layers were dried ($Na_2SO_4$), filtered and concentrated to dryness on a rotary evaporator to afford 1-(1-(4-methylbenzyl-1-sulfonyl)-1H-imidazol-4-yl)ethan-1-amine (400 mg, 66%) as sticky yellow liquid. ESIMS m/z (M+1): 266.3.

Ethyl 3-(1-aminoethyl)-1H-pyrazole-5-carboxylate

Titanium (IV) isopropoxide (6.2 g, 21.98 mmol) was added to a stirred solution of ethyl 3-acetyl-1H-pyrazole-5-carboxylate (2.0 g, 10.89 mmol) in 7N methanolic ammonia (20 mL, 10 vol) at 0° C. and stirred at room temperature for 4 h. Then, sodium borohydride (0.82 g, 21.78 mmol) was added at 0° C. and stirred at room temperature for 4 h. Completion of the reaction was confirmed by UPLC, then organic solvent was concentrated under reduced pressure. Reaction mixture was quenched with saturated sodium bicarbonate solution (50 mL) and extracted with ethyl acetate (2×100 mL). The combined organic layer was washed with brine, dried over $Na_2SO_4$ and concentrated to afford ethyl 3-(1-aminoethyl)-1H-pyrazole-5-carboxylate (3f) (1.1 g, 55%) as yellow liquid. $^1$H NMR (400 MHz, DMSO-$d_6$.$D_2O$) δ (ppm): 6.62 (s, 1H), 4.24 (q, 2H, J=7.0 Hz), 3.99-4.02 (m, 1H), 1.24-1.29 (m, 6H, J=7.0 Hz); ESIMS m/z (M+1): 184.2.

Example 2: Method Used to Assess the Solubility of Compounds of the Invention

The solubility and metabolic stability of the compounds of the invention was assessed according to the protocol detailed described in Phillips et al., 2015, supra and presented in Table 1 below in comparison with DSM 265 which has the following structure:

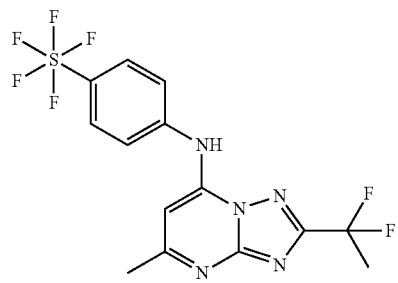 [SMILES: Cc1cc(Nc2ccc(S(F)(F)(F)(F)F)cc2)n2nc(C(C)(F)F)nc2n1]

TABLE 1

| Compound | Human $Cl_{int}$ (μL/min/mg protein) | FaSSIF Solubility pH 6.5 5 h, μg/ml |
|---|---|---|
| 8 | 66 | nd |
| 11 | 40 | nd |
| 14 | <7 | nd |
| 17 | 16 | nd |
| 20 | 35 | nd |
| 29 | 29 | 9.9 |
| 32 | 20 | 34 |
| 35 | 20 | 60 |
| 2 | 11 | 890 |
| 26 | 12 | 353 |
| DSM265 (comparative) | <7 | 5.1 |

Those data support that solubility of compounds of the invention is significantly improved over DSM265. Further, compound 14 is particularly metabolically stable.

Example 3: Activity of Compounds Against *Plasmodium* and Mammalian DHODH Showing that Compounds have Selective Activity Towards the *Plasmodium* Enzymes Protein Expression and Purification. BL21-DE3 *E coli* phage-resistant cells containing His$_6$-tagged DHODH-pRSETb (N-terminal tag)(Pf and PvDHODH), pET22b C-terminal tag (human) or pET-28b C-terminal tag (rat, mouse and dog) constructs were grown and harvested using the appropriate antibiotic and protein was purified using a HisTrap HP column followed by gel filtration as previously described (Coteron et al., 2011, J Med Chem, 54 (15), 5540-61; Phillips, et al 2015, supra; White et al., 2019, ACS Infect Dis, 5 (1), 90-101. The concentration of purified DHODH was determined based on FMN absorbance at 454 nm (ε445=12.5 mM$^{-1}$ cm$^{-1}$)(Malmquist et al., 2008, Biochemistry, 47 (8), 2466-75).

DHODH Kinetic Analysis. The 50% inhibitory concentration ($IC_{50}$) for the described compounds was determined using the 2,6-dichloroindophenol (DCIP) assay to monitor the DHODH reaction rate at 25° C. in assay buffer (100 mM HEPES, pH 8.0, 150 mM NaCl, 10% glycerol, 0.1% Triton X-100 reduced, 20 μM $CoQ_D$, 200 μM L-DHO and 5-20 nM enzyme) as described in Malmquist et al., 2008, supra. Inhibitor stocks (100 mM) were prepared in DMSO in amber bottles. A 3-fold dilution series was generated in DMSO from these stocks and then dispensed into assay buffer via a 1/100 dilution to generate a final concentration range of 0.001-100 μM (1% DMSO final). Data were collected using triplicate technical replicates and where indicated additional biological replicates were collected (the number of biological replicates is provided in parenthesis). $IC_{50}$'s were determined by fitting the data to log (inhibitor) vs. response equation Y=Bottom+(Top−Bottom)/(1+10^((X−Log $IC_{50}$))) in GraphPad Prism. Compounds in the invention show potent activity versus *P. falciparum* DHODH but importantly, unlike DSM265, they show equivalent activity on *P. vivax* and *P. falciparum* DHODH (see above methods for protein purification and enzyme assays)(Table 2). Furthermore, the compounds of the invention do not inhibit any of the tested mammalian DHODHs including human DHODH and they also retain their selectivity versus DHODHs from important toxicologic models (including mouse, rat and dog). DHODH inhibition data for key compounds is provided in the Table 2 below.

Table 3 below shows the in vitro $EC_{50}$s (μM) against different strains of *P. falciparum*, namely 3D7 and Dd2. Using the above described *P. falciparum* growth and inhibition assays

TABLE 3

| Compound | $EC_{50}$ (μM) 3d7 | Dd2 |
|---|---|---|
| 5 | 0.039 | nd |
| 8 | 0.0013, 0.0011 | nd |
| 11 | 0.0040 ± 0.0015 | nd |

TABLE 2

| Compound | *P. falciparum* DHODH ($IC_{50}$ μM) | *P. vivax* DHODH ($IC_{50}$ μM) | Human DHODH ($IC_{50}$ μM) | Mouse DHODH ($IC_{50}$ μM) | Rat DHODH ($IC_{50}$ μM) | Dog DHODH ($IC_{50}$ μM) |
|---|---|---|---|---|---|---|
| 5 | 0.11 | 0.061 | >100 | nd | nd | nd |
| 8 | 0.034 | 0.032 | >100 | nd | nd | nd |
| 11 | 0.057 | 0.041 | >100 | nd | nd | nd |
| 14 | 0.14 ± 0.057 | 0.17 | >100 | >100 | >100 | >100 |
| 17 | 0.085, 0.060 | 0.043 | >100 | nd | nd | nd |
| 20 | 0.076, 0.095 | 0.041 | >100 | nd | nd | nd |
| 29 | 0.025 ± 0.0071 | 0.012 | >100 | >100 | >100 | >100 |
| 32 | 0.047 ± 0.0079 | 0.043 | >100 | >100 | >100 | >100 |
| 35 | 0.050 ± 0.0065 | 0.041, 0.036 | >100 | >100 | >100 | >100 |
| 2 | 0.098 ± 0.041 | 0.052 ± 0.032 | >100 | >100 | >100 | >100 |
| 26 | 0.096 ± 0.047 | 0.074 ± 0.0036 | >100 | nd | nd | nd |
| 25 (racemate of 26) | 0.14 | 0.26 | >100 | >100 | >100 | >100 |
| DSM265 (comparative) | 0.030 ± 0.014 | 0.072 ± 0.028 | >100 | 2.3 ± 0.64 | 2.6 ± 0.39 | 16 ± 6.5 |

*error is standard error of the mean for n > 3 independent biological experiments.

Example 4: Anti-Malarial In Vitro and In Vivo Efficacy of Compounds According to the Invention The in vitro of compounds of the invention was tested against chloroquine-resistant (Dd2) and chloroquine-sensitive (3D7) strains of *P. falciparum* in vitro as described below.

*P. falciparum* growth and inhibition assays. *P. falciparum* 3D7 cells were grown in RPMI media supplemented with 0.5% albuMAX I, human red blood cells to 0.5% hematocrit and 0.5% parasitemia as described (Coteron et al., 2011, *J. Med. Chem.*, 54, 5540-5561). DSMO inhibitor stocks (as above) were diluted in DMSO using a 2 or 3-fold dilution series and then dispensed into media at 10× the final concentrations. A second step into media led to final inhibitor concentrations ranging from 0.001-30 μM and a final DMSO concentration of 0.2%. Parasites in the presence of either DMSO controls or DHODH inhibitors were grown at 37° C. for 72 h before growth was assessed using the SYBR Green method (as described in Bennett et al., 2004, *Antimicrob Agents Chemother*, 48 (5), 1807-10 with minor modifications as described in Deng, 2014, *J Med Chem*, 57 (12), 5381-94), which measures fluorescence (ex./em. 485/535 nm) as the output. Data were collected using triplicate technical replicates and where indicated additional biological replicates were collected (the number of biological replicates is provided in parenthesis). The 50% effective concentration ($EC_{50}$) was determined by fitting data to log (inhibitor) vs. response equation Y=Bottom+(Top−Bottom)/(1+10^((X−Log $IC_{50}$))) equation in GraphPad Prism.

TABLE 3-continued

| Compound | $EC_{50}$ (μM) 3d7 | Dd2 |
|---|---|---|
| 14 | 0.010, 0.0088 | nd |
| 17 | 0.0052 ± 0.0024 | nd |
| 20 | 0.022 ± 0.013 | nd |
| 29 | 0.0069 ± 0.0046 | 0.0064 ± 0.0038 |
| 32 | 0.0040, 0.0030 | 0.0030, 0.0020 |
| 35 | 0.0082 ± 0.0067 | 0.0070 ± 0.0036 |
| 2 | 0.013 ± 0.0055 | 0.022 ± 0.0068 |
| 26 | 0.0064 ± 0.0039 | nd |
| DSM265 (comparative) | 0.0060 ± 0.0019 | 0.0060 ± 0.0026 |

Error represents the standard deviation for 3 or more biological experiments.

Compounds from this invention were also tested on clinical isolates of *P. falciparum* and *P. vivax* parasites in ex-vivo assays. Importantly this data showed efficacy was equivalent for *P. falciparum* and *P. vivax* parasites, providing a significant improvement over DSM265 (Table 4).

*P. falciparum* and *P. vivax* ex vivo assays using clinical isolates. The assay is based on the inhibition of schizont maturation relative to drug-free controls (Russel et al., 2003, *Antimicrob Agents Chemother*, 47; 170-173). This assay uses a human serum based media and thus the percent of protein bound drug is higher than in the above described albumax assay, leading to higher apparent $EC_{50}$ values. *P. falciparum* and *P. vivax* isolates were collected from patients recruited at the Centre of Malaria Control (CEPEM) in the city of Porto Velho, state of Rondônia, in the Brazilian Western Amazon. This study was approved by the Ethics Committee from the Centro de Pesquisa em Medicina Tropical-CEPEM-Rondônia (CAAE 61442416.7.0000.0011). Data for DSM265 were collected in a separate study from patients visiting a clinical site in Indonesia and were previously reported (Phillips et al., 2016, *ACS Infec Dis*, 2:945-957). Table 4 below compares *P. vivax* and *P. falciparum* ex vivo susceptibility to compounds of the invention and to DSM 265.

TABLE 4

| Compound | *P. falciparum* $EC_{50}$ (µM) | *P. vivax* $EC_{50}$ (µM) |
|---|---|---|
| 2 | 0.13 | 0.12 |
| 26 | 0.060 | 0.044 |
| DSM265 (Comparative) | 0.19 | 0.92 |

The in vivo efficacy was tested in the humanized SCID mouse model as described below: Mice engrafted with human erythrocytes (>40% of human erythrocytes in peripheral blood) were intravenously infected with parasitized red blood cells 72 h before treatment inception. At this point (Day 1 of study), mice had between 1-2% of parasitemia on average and the mice were randomly allocated to selected treatments. The effect of treatment on parasitemia was assessed by measuring the percentage of infected erythrocytes in peripheral blood every 24 h until parasitemia was below the selected limit of quantitation (usually 0.01%). During the study, samples of peripheral blood were taken from mice to measure the concentration of compounds and/or their metabolites. The parasitemia in mice was regularly measured up to day 60 of experiment to check the presence circulating parasitized human erythrocytes. Methods for the SCID mouse efficacy model are described in Angulo-Barturen et al., 2008, *Plos One*, 21; 3(5):e2252; Jiménez-Diaz et al., 2009, *Antimicrob Agents Chemother.*, 53(10): 4533-4536; Jiménez-Diaz et al, *Plos One* 8(6): e66967; Jiménez-Diaz et al. 2009, Cytometry A., (3):225-35.

Compounds were dosed b.i.d. (twice daily) for 6 days at the indicated dose levels and as a control DSM265 was dosed in the same model. Efficacy was achieved at a similar dose for all three compounds listed in Table 5 below. The blood level of compound required for efficacy at the 50 mgs/kg b.i.d. dose was lower for compound 26 than for compound 2, suggesting it is the more potent of the two in vivo. This study suggests that the compounds of the invention show equivalent efficacy to DSM265.

TABLE 5

| Compound | DSM265 (comparative) | 2 | 26 |
|---|---|---|---|
| $ED_{90}$ (mg/kg) | 16.7 | 25.6 | <50 mg/kg bid |
| $AUCED_{90}$ (µM · h/day) | 35.4 | 35.6 | <100 |
| $CED_{90}$ (µM/day) | 1.48 | 1.48 | <4 |
| DOR (50 mg/kg dose) | 21 | 22 | 22 |

$ED_{90}$: concentration required to clear 90% of parasites as measured 24 h post the final dose on day 7. $CED_{90}$: estimated average blood concentration that induces no net parasite growth.

The day of recrudescence (DoR) was calculated for the mice that showed a decline of parasitemia below parasitemia at treatment inception (PO) and a subsequent growth up to PO. DoR was estimated by linear interpolation of % parasitemia the day before the rise to PO and the % parasitemia the day after reaching PO.

Altogether, those data support that the compounds of the invention have anti-*Plasmodium* activity that is equivalent to the clinical candidate DSM265 while showing improved stability and species selectivity, namely equivalent activity on the two most important human *Plasmodium* species, *P. falciparum* and *P. vivax*.

The invention claimed is:
1. A compound according to Formula (I):

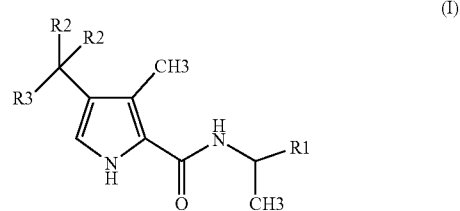

(I)

wherein $R_1$ is an optionally substituted 5-membered heterocycle; $R_2$ is H or both $R_2$ are joined to form an optionally substituted cyclopropyl; $R_3$ is selected from an optionally substituted monocyclic aryl and an optionally substituted heteroaryl; pharmaceutically acceptable salts, hydrates, tautomers, racemic mixtures, or optically active forms thereof, wherein the term substituted refers to a group substituted with from 1 to 5 substituents selected from the group consisting of $C_1$-$C_6$ alkyl, $C_2$-$C_6$ alkenyl, $C_2$-$C_6$ alkynyl, $C_3$-$C_8$-cycloalkyl, heterocycloalkyl, $C_1$-$C_6$ alkyl aryl, $C_1$-$C_6$ alkyl heteroaryl, $C_1$-$C_6$ alkyl $C_3$-$C_8$-cycloalkyl, $C_1$-$C_6$ alkyl heterocycloalkyl, acyl, amino, amide, aminosulfonyl, ammonium, acyl amino, aminocarbonyl, aryl, heteroaryl, sulfinyl, sulfonyl, sulphonamide, alkoxy, alkoxy carbonyl, carbamate, sulfanyl, halogen, trihalomethyl, cyano, hydroxy, mercapto, and nitro.

2. The compound according to claim 1, wherein $R_1$ is an optionally substituted triazole.

3. The compound according to claim 1, wherein $R^1$ is an optionally substituted pyrazole.

4. The compound according to claim 1, wherein $R^1$ is an optionally substituted imidazole.

5. The compound according to claim 1, wherein $R^1$ is an optionally substituted isoxazole.

6. The compound according to claim 1, wherein $R_2$ is H.

7. The compound according to claim 1, wherein both $R_2$ are joined to form an optionally substituted cyclopropyl.

8. The compound according to claim 1, wherein $R^3$ is an optionally substituted monocyclic aryl.

9. The compound according to claim 1, wherein $R^3$ is an optionally substituted heteroaryl.

10. The compound according to claim 1, wherein $R^3$ is an optionally substituted pyridinyl.

11. The compound according to claim 1, selected from the following group:

3-methyl-N-(1-(1H-1,2,4-triazol-3-yl)ethyl)-4-(1-(6-(trifluoromethyl)pyridin-3-yl) cyclopropyl)-1H-pyrrole-2-carboxamide;

N-(1-(1H-1,2,4-triazol-3-yl)ethyl)-4-(3-fluoro-4-(trifluoromethyl)benzyl)-3-methyl-1H-pyrrole-2-carboxamide;

N-(1-(1H-pyrazol-4-yl)ethyl)-3-methyl-4-(1-(6-(trifluoromethyl)pyridin-3-yl)cyclopropyl)-1H-pyrrole-2-carboxamide;

3-methyl-N-[1-(5-methyl-1H-pyrazol-3-yl)ethyl]-4-{1[6-(trifluoromethyl)pyridine-3-yl]cyclopropyl}-1H-pyrrole-2-carboxamide;

3-(1-(3-methyl-4-(1-(6-(trifluoromethyl)pyridin-3-yl)cyclopropyl)-1H-pyrrole-2-carboxamido)ethyl)-1H-pyrazole-5-carboxamide;

N-(1-(5-cyano-1H-pyrazol-3-yl)ethyl)-3-methyl-4-(1-(6-(trifluoromethyl)pyridin-3-yl)cyclopropyl)-1H-pyrrole-2-carboxamide;

N-(1-(1H-imidazol-4-yl)ethyl)-3-methyl-4-(1-(6-(trifluoromethyl)pyridin-3-yl)cyclopropyl)-1H-pyrrole-2-carboxamide;

4-(1-(6-(difluoromethyl)pyridin-3-yl)cyclopropyl)-3-methyl-N-(1-(1H-1,2,4-triazol-3-yl) ethyl)-1H-pyrrole-2-carboxamide;

4-{1-[3-cyano-4-(trifluoromethyl)phenyl]cyclopropyl-3-methyl-N-[1-(1H-1,2,4-triazol-3-yl) ethyl]-1H-pyrrole-2-carboxamide;

3-methyl-N-(1-(5-methylisoxazol-3-yl)ethyl)-4-((6-(trifluoromethyl)pyridin-3-yl)methyl)-1H-pyrrole-2-carboxamide;

3-methyl-N-(1-(1H-pyrazol-4-yl)ethyl)-446-(trifluoromethyl)pyridin-3-yl)methyl)-1H-pyrrole-2-carboxamide; and 3-methyl-N-(1-(1-methyl-1H-pyrazol-4-yl)ethyl)-4-((6-(trifluoromethyl)pyridin-3-yl)methyl)-1H-pyrrole-2-carboxamide; as well as pharmaceutically acceptable salts, hydrates, tautomers, racemic mixtures, and optically active forms thereof.

12. A pharmaceutical formulation containing at least one compound according to claim 1 and a pharmaceutically acceptable carrier, diluent or excipient thereof.

13. A pharmaceutical composition according to claim 12, further comprising an antimalarial co-agent.

14. A pharmaceutical composition according to claim 13, wherein the co-agent is selected from artemisinin or an artemisinin and its derivatives, artemether, dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-, (1' R,3'S)-,(2-(1,1-difluoroethyl)-5-methyl-N-[4-(pentafluoro-λ$^6$- sulfanyl)phenyl]-[1,2,4]triazolo[1,5-a]pyrimidin-7-amine), Morpholine,4-[2-(4-cis-dispiro[cyclohexane-1,3 '-[1,2,4]trioxolane-5',2"-tricyclo [3.3.1.1$^{3,7}$]decan]-4-ylphenoxy)ethyl]-, [3,3 '-Bipyridin]-2-amine, 5-[4-(methylsulfonyl)phenyl]-6'-(trifluoromethyl)-, Ethanone, 2-amino-1-[2-(4-fluorophenyl)-3-[(4-fluorophenyl)amino]-5,6-dihydroimidazo[1,2-a]pyrazin-7(8 H)-yl]-.

15. A method for preparing a compound of Formula (Ia), wherein both $R_2$ are joined to form an optionally substituted cyclopropyl, said method comprises transforming a compound according to Formula (X) into a compound of Formula (Ia), as follows:

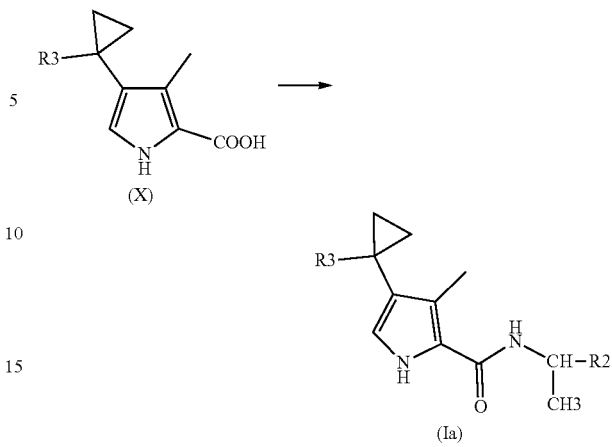

wherein $R^1$ and $R^3$ are defined in claim 1 and said transforming comprises reacting a compound of Formula (X) with a compound containing an amine group to form a compound of formula (Ia).

16. A method for preparing a compound of Formula (Ib), wherein both $R_2$ are H, said method comprises transforming a compound according to Formula (XI) in a compound of Formula (Ib) as follows:

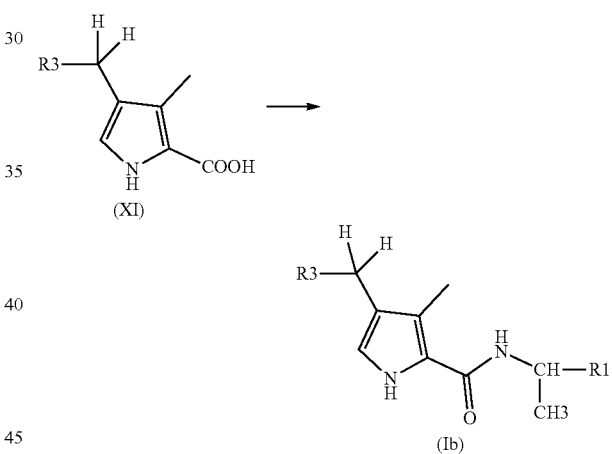

wherein $R^1$ and $R^3$ are defined in claim 1 and said transforming comprises reacting a compound of Formula (XI) with a compound containing an amine group to form a compound of formula (Ib).

17. An intermediate of Formula (X)

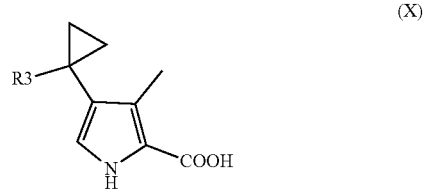

wherein $R^3$ is defined in claim 1.

18. An intermediate of claim 17, selected from the following group:

3-methyl-4-(1-(6-(trifluoromethyl)pyridin-3-yl)cyclopropyl)-1H-pyrrole-2-carboxylic acid;

4-(3-fluoro-4-(trifluoromethyl)benzyl)-3-methyl-1H-pyrrole-2-carboxylic acid; and 4-(1-(6-(difluoromethyl)pyridin-3-yl)cyclopropyl)-3-methyl-1H-pyrrole-2-carboxylic acid.

19. An intermediate of Formula (XI)

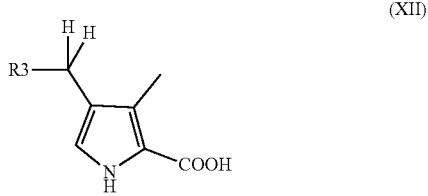
(XII)

wherein $R^3$ is an optionally substituted heteroaryl or an optionally substituted pyridinyl.

20. An intermediate according to claim 19, wherein said intermediate is 3-methyl-4-((6-(trifluoromethyl)pyri di n-3-yl)methyl)-1H-pyrrole-2-carboxylic acid.

21. A method for arresting the development of malaria in a patient, said method comprising administering a compound according to claim 1 or a pharmaceutical formulation thereof in a patient in need thereof.

22. The method according to claim 21, wherein the said compound is administered in combination with an antimalarial co-agent.

23. The compound according to claim 1, wherein $R_1$ is an optionally substituted triazole, an optionally substituted 1, 2, 4 triazole, an optionally substituted pyrazole, and optionally substituted pyrazole-4-yl, 1H-pyrazol-4-yl, 1-methyl-pyrazol-4-yl, an optionally substituted pyrazole-3-yl, 5-methyl-1H-pyrazol-3yl, 5-cyano-1H-pyrazol-3-yl, an optionally substituted imidazole, an optionally substituted imidazole-4-yl, imidazole-4-yl, an optionally substituted isoxazole, an optionally substituted is oxazol-3-yl, or 5-methylisoxazol-3-yl.

24. The compound according to claim 1, wherein $R_3$ is an optionally substituted phenyl, 3-fluoro-4-(trifluoromethyl) phenyl, an optionally substituted heteroaryl, an optionally substituted pyridinyl, an optionally substituted pyridin-3-yl, trifluoromethyl pyridin-3-yl, or di-fluoro-methyl pyridin-3-yl.

* * * * *

UNITED STATES PATENT AND TRADEMARK OFFICE
CERTIFICATE OF CORRECTION

PATENT NO. : 11,903,936 B2
APPLICATION NO. : 17/787378
DATED : February 20, 2024
INVENTOR(S) : Margaret Phillips et al.

It is certified that error appears in the above-identified patent and that said Letters Patent is hereby corrected as shown below:

In the Specification

Column 18,
Line 17, "per million (6)" should read --per million ($\delta$)--.

Column 21,
Line 40, "in THE" should read --in THF--.

Column 23,
Line 66, "in THE" should read --in THF--.

Column 24,
Line 45, "in THE" should read --in THF--.

Column 25,
Line 9, "in THE" should read --in THF--.

Column 30,
Line 64, "in THE" should read --in THF--.

Column 32,
Line 5, "THE" should read --THF--.
Line 53, "in THE" should read --in THF--.

Column 33,
Line 13, "in THE" should read --in THF--.

Signed and Sealed this
Twenty-fourth Day of September, 2024

Katherine Kelly Vidal
*Director of the United States Patent and Trademark Office*

CERTIFICATE OF CORRECTION (continued)

U.S. Pat. No. 11,903,936 B2

Column 39,
Lines 3-4, "3-methyl-N-(1-(1H-pyrazol-4-yl)ethyl)-446-(trifluoromethyl)pyridin-3-yl)methyl)-1H-pyrrol e-2-carboxamide," should read --3-methyl-N-(1-(1H-pyrazol-4-yl)ethyl)-4-((6-(trifluoromethyl)pyridin-3-yl)methyl)-1H-pyrrole-2-carboxamide,--.
Line 6, "(400 MHz, CD₃OD)67 (ppm):" should read --(400 MHz, CD₃OD) δ (ppm):--.

Column 40,
Lines 1-3, "3-methyl-N-(1-(1-methyl-1H-pyrazol-4-yl)ethyl)-4-((6-(trifluoromethyl)pyri din-3-yl)methyl)-1 H-pyrrole-2-carboxamide," should read --3-methyl-N-(1-(1-methyl-1H-pyrazol-4-yl)ethyl)-4-((6-(trifluoromethyl)pyridin-3-yl)methyl)-1H-pyrrole-2-carboxamide,--.
Line 34, "in THE" should read --in THF--.

In the Claims

Column 47,
Lines 1-3, "N-(1-(1H-pyrazol-4-yl)ethyl)-3-methyl-4-(1-(6-(trifluoromethyl)pyri din-3-yl)cyclopropyl)-1H-pyrrole-2-carboxamide;" should read --N-(1-(1H-pyrazol-4-yl)ethyl)-3-methyl-4-(1-(6-(trifluoromethyl)pyridin-3-yl)cyclopropyl)-1H-pyrrole-2-carboxamide;--.
Lines 8-10, "3-(1-(3-methyl-4-(1-(6-(trifluoromethyl)pyri din-3-yl)cyclopropyl)-1H-pyrrol e-2-carboxamido)ethyl)-1H-pyrazole-5-carboxamide;" should read --3-(1-(3-methyl-4-(1-(6-(trifluoromethyl)pyridin-3-yl)cyclopropyl)-1H-pyrrole-2-carboxamido)ethyl)-1H-pyrazole-5-carboxamide;--.
Lines 21-23, "4-{1-[3-cyano-4-(trifluoromethyl)phenyl]cyclopropyl-3-methyl-N-[1-(1H-1,2,4-triazol-3-yl) ethyl]-1H-pyrrole-2-carboxamide;" should read --4-{1-[3-cyano-4-(trifluoromethyl)phenyl]cyclopropyl}-3-methyl-N-[1-(1H-1,2,4-triazol-3-yl) ethyl]-1H-pyrrole-2-carboxamide;--.
Lines 28-29, "3-methyl-N-(1-(1H-pyrazol-4-yl)ethyl)-446-(trifluoromethyl)pyridin-3-yl)methyl)-1H-pyrrole-2-carboxamide;" should read --3-methyl-N-(1-(1H-pyrazol-4-yl)ethyl)-4-((6-(trifluoromethyl)pyridin-3-yl)methyl)-1H-pyrrole-2-carboxamide;--.
Lines 31-33, "3-methyl-N-(1-(1-methyl-1H-pyrazol-4-yl)ethyl)-4-((6-(trifluromethyl) pyri din-3-yl)methyl)-1H-pyrrole-2-carboxamide;" should read --3-methyl-N-(1-(1-methyl-1H-pyrazol-4-yl)ethyl)-4-((6-(trifluoromethyl)pyridin-3-yl)methyl)-1H-pyrrole-2-carboxamide;--.

Column 49,
Lines 20-21, "3-methyl-4-((6-(trifluromethyl)pyri di n-3-yl)methyl)-1H-pyrrole-2-carboxylic acid" should read --3-methyl-4-((6-(trifluoromethyl)pyridin-3-yl)methyl)-1H-pyrrole-2-carboxylic acid--.